(12) United States Patent
Belknap et al.

(10) Patent No.: US 8,927,702 B2
(45) Date of Patent: Jan. 6, 2015

(54) SOLANUM BULBOCASTANUM POLYUBIQUITIN BUL409 PROMOTER AND USES THEREOF

(75) Inventors: William R. Belknap, Albany, CA (US); Sophie S. Chang, Oakland, CA (US); David R. Rockhold, El Cerrito, CA (US); Nathaniel T. Taylor, San Leandro, CA (US); Kent F. McCue, El Cerrito, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1135 days.

(21) Appl. No.: 11/820,543

(22) Filed: Jun. 19, 2007

(65) Prior Publication Data

US 2009/0019562 A1    Jan. 15, 2009

(51) Int. Cl.
*C12N 15/82* (2006.01)
*C12N 15/87* (2006.01)
*A01H 5/00* (2006.01)

(52) U.S. Cl.
CPC .................................. *C12N 15/8216* (2013.01)
USPC ........ 536/24.1; 800/287; 800/279; 435/320.1

(58) Field of Classification Search
None
See application file for complete search history.

(56) References Cited

U.S. PATENT DOCUMENTS 6,018,102 A    1/2000    Garbarino et al.

OTHER PUBLICATIONS

Evans et al 1992, Plant Mol. Biol. 20:1019-1028.*
Fourgoux-Nicol et al. 1999, Plant Molecular Biology 40:857-872.*
Kim et al. 1994, Plant Molecular Biology 24: 105-117.*
Garbarino, J.E., Rockhold, D.R., and Belknap, W.R., "Expression of stress-responsive ubiquitin genes in potato tubers," Plant Molecular Biology (1992) 20:235-244.
Garbarino, J.E. and Belknap, W.R., "Isolation of a ubiquitin-ribosomal protein gene (ubi3) from potato and expression of its promoter in transgenic plants" Plant Molecular Biology (1994) 24:119-127.
Garbarino, J.E., Oosumi, T., and Belknap, W.R., "Isolation of a Polyubiquitin Promoter and Its Expression in Transgenic Potato Plants" Plant Phyisol (1995) 109:1371-1378.
Song, J., Dong, F. and Jiang, J., "Construction of a bacterial artificial chromosome (BAC) library for potato molecular cytogenetics research" Genome (2000) 43:199-204.

* cited by examiner

*Primary Examiner* — Li Zheng
(74) *Attorney, Agent, or Firm* — Elizabeth R. Sampson; Lesley Shaw; John Fado

(57) ABSTRACT

The present invention relates to isolated *Solanum Bulbocastanum* Bul409 promoter sequences and uses thereof. An exemplary embodiment provides an isolated plant Bul409 promoter comprising a nucleic acid sequence that is at least about 90% identical to nucleotides 1-771 of SEQ ID NO:1, wherein the promoter sequence is capable of controlling transcription in a plant. Other exemplary embodiments provide a method for making a transgenic plant, wherein the method comprises transforming a plant, plant part, or plant cell with an expression vector comprising isolated plant Bul409 promoter operably linked to a heterologous nucleic acid sequence, wherein the isolated plant Bul409 promoter is capable of controlling transcription of the heterologous nucleic acid in a plant, and a transgenic plant made by the method and decendants thereof.

18 Claims, 14 Drawing Sheets

```
ACTTACCTCTTATATAAAAAAGAAAAAGTGTTTCTAATATATACTCAATTTAAATAAAA
TATTTTCAATCAAATTTAGATAACAAATACTTATCAATATGAGGTCAATAACAATAAAA
AAATAATGTAAAAAAAAGGAGCAATACATAATATAAGAAAAAAGATTAAAGTGCGATT
ATCAACGAGTATTATACCCTAATTTGCTAATATTTAAACTCTTATATTTAAGGTTATGT
TCACAATATACTTAAAAAGCGCTATATTAGAGCATATATTAATTAATAAAAAGAAAAT
GCTAAATGATCAAAAAAATTAGATAGAAAATTAAGAAAATTATAATATTTTTTATTTT
AAAATAAATTGATATATTCTTTATTTTTAGTTAAAATGTATTAAAGTTAAAGAATAA
AAATATTTTAAAAAATAAAATAACATAAATAAAATATCATTCTAATTAAATTCAGACCA
AATTTTTTCCCCAGATTTTGGCCAATACCTAAAATAAAATTAAGTTATTTTAGTATAT
TTTTTTACATTGACCTACATTTTTCTAGTTTTTTCTAAAGGAGCGTGTAAGCGTCAACC
TCATTCTCCTAATTTTCCCCACCACATAAATAAAAAGAAACGGTAGCTTTTGCGTGTTG
TTTTGCTACACTACACCTCATTATTACACGTGTCATCATATAATTGGCTAACCCTATGA
GGCGGTTTCGTCTAGAGTCGGCCATGCCATCTATAAAAGGAACCTTTCTGCACCTCATT
TTTTCATCTTCTATCTGACTTCTATTATAATTTCTCTCAATTGCCTTTAAATTTCTCTT
TCAAGGTTAGAAATCTTCTCTATTTTTTGGTTTTTGTCTGTTTAGATTCTCGAATTAGC
TAAGCAGGTGCTGTTAAAGCCCTAAAATTTGAGTTTTTTTCCGTTGTTTTGATGAAAA
AGCCCCTAATTTGAGTTTTTTTCCGTCGATTTGATGCCAAAGGTTTAAAATTAGAGTTT
TTTCGTCGGTTTGATTCTAAAGGCCCAAAATGTGGGGTTTTCCGGGTGATTTGATGATA
ATGCCCTAGAATTTGAGTTTTTTTATGGTGGTTTGATGAAAAAGGTCTTGAATTTGATT
TTTTTTTTCCGGTTGATTTGATGAAAAAGCCCTAGAATTTGTGATTTTTCGTCGGTTTG
ATTCTAAAGCCCTAAAATTTGAGGTTTTCCGGTTGTTTTGATGAAAAAGCCCTAAAATT
TGAGTTTTTTCCCCGTGTTTTAGATTGTTTGGTTTTAATTCTCGAATCAGTTAATCAGG
GAGTGTGAAAAGCCCTATAATTTGAGTTTTTTTCGTTGTTCCGATTGTTGTTTTATGA
CTTTGCAGATGCAGATCTTTGTGAAACTCTCACCGGAAAGACCATCACCCTAGAGGTG
GAACGTTCTGATACAATCGACAACGTTAAGGCTGAGATTCAGGATAAGGAAGGAATTCC
CCCGGATCAGCAAAGGCTTATCTTCGCCGGAAAGCAGTTGGAGGACGGACGTACTCTAG
CTGATTACAACATCCAGAAGGAGTCTACCCTCCATTTGGTTCTCCGTCTACGTGGTGGT
```

FIG. 1

```
AAGCTTATAAGATTACAAACAAAAAATCAAATACAAAGTAGAATTCTAATAAAAAGGGT
AGGAAAATCGATACAAATAAAATTATTAAAAATGAATAAGGCAACAATGAAAAAAAAAT
AAAGGTAATGAAAATCACACCAAACCTTTGTTATATAAAGAAAAAAGACAATTTTCATC
TTACAAAAAAGCAACTTCAATATACACCAAGTTGCATTAATGCTTAATGCTTGGACAGT
TGAGTTAATATTTAAGTTAAAGACAATTATTATTAAAAAACTAAAATAAGAGAGGTAAA
CATAATATATTATAAATTACCATGAAAGTAAAGTATTAGGAAATTAAACTTGAAGGGTA
GTTTGTACAATTATCTCTTTTACCTTTTGGTTATAATAATTGTAGAAAAATTAATTACT
TGAATGACTTTATAAAAGAAAATTCATTAAATTGAGTGGCTTTATTGATACACACAAGT
TGATTGACTTTCTCAGATGGTAAGTGAAAAGTGCAGTGTACTATGTCTTGCATCTGCTT
AGGCTCGTTAAATAATAGAGATATTACTTAGTTGTGAGATTAGGGAGTTAATCTCATTG
TTGTGGTGTAAACTTTGCTTTACTTTTGCTTGAGAAGATTAGTAAAACAGTTTGAAAA
TTCTTGTGAGATAGGTCATGATTTTACTTCTTGAGCAAGGAGATTTTCACATAAAAAT
TTTGTGTCTATTTTATATTGTGATATTTACTTTATGCATTATTATTCTGCTGAGGGACA
TGATCCCGTGGTCACTTATGGACGCATACATACCAACAAATTTGTATATCTCAAAGTTA
TCGACGTCGTTGCTTTATCATCACAATTCACAACTTCTTTACTTAAAATCCGTGCCCAC
CTTGAATGGATATGCATTTTTCTAACTTTTAAAAGACACCACTTGCAACAAAAAAAGAA
TCTTTCATTTTTTAAAAAAATTATTAAATACAATATAATATAAAGTAGGCCCATAAAAA
TATCTTAATCAAGTAAATTCAAATTGGGGTAGTTGACAAAAAAGAAAAAAAATAGCAAA
CAAAAGCAAGTGTCAAGTGGATGCATAACAGTTCCCCTAGTTTTGAAAGAAGAGGTCAA
TTATGCCGCTCTTAACGTAACGCTCCACGAAGAAGCCGTTTGCACCTAAAACATCTACT
AGCCCACAGTAACGTATGGGAAGAATTTATTCGCATCGGATAGTTTATATTAAACTAA
TATAATCTTTTATTATTATGTGATTTAACAAAGTAAAATACATGTTAATTAATTAAAAT
TAAGTAAAATGAACTGTAAATTTAAATATATGGCGTGCATGTATTGAATTGACGTATAC
ACCTGGTCCGGATAAGTTTTACCCTAATATAAATAGTAATCGTCAAAGTAAGCGGTGTA
GTATATACGATCTTTAGTACATGGTGTAGTAAATACGATTTTTGAATAAAAAACATTTC
TTTCTAAATAACTATTTAACATAAATTTAAAATGATCAAACTTTAATATAAATATTAGA
TGTCAAATAAAAGAATTAAAAGAAAATATGAATAGTAGATTTAGACTATTTGTTGAGT
CTCATTTATCGAAAATATTTTTTTTTAGGTATTCTATTTTTTCTAAACGTCATTTTGA
GGAACTACATACCATGGATATAAAAAAGGGACAAAAATAATACAATTTTTGTTCAACTA
ATCTTTTTTTTTTTTTTCGCTTTTAAAAAAGAGGAGAGTGATGGTTAATAATTAAATA
ATGAAAAGAAGGAAAGAAAATTTTCGAATAAAAATGTCAAAAGAGAAAAAAGAGAGG
GAGTAATCATTGATCAACTTTATACAGAATCAAGTACCCCAATTTGATTTTTCATGGAT
ATCAAAATTTACAAGAATTTATTAAAATATAGATATCGGGTAAATTTATTAACAAGATT
TGAACATATAAATAAAAATTATGTAATATTTCAACTCTAAATAAACTAATATTTGAAAT
CTCAAATTTATGATTTTAAATTTACTTTATATCCAAGACAATTTCAGCTTAAAAAGGT
TTATTAATATTTACATTAGTTTTGTTGATGAGGATGACAAGAATTTGGTCATCAACTAC
ATATACCCAAATTGAATAGTAAGCAACTTAATGTTTTTCATAATGATAATATGACAGAC
ACAAAAAAAAAACCATTCATTATTCACATAGATTGATTTTTATATGCAATATAATAAT
AATAATAATAATAATAATAATAATAATAATAATAATATATATATATATATATTTCTTAT
AAAGCAAGAGGTCAATTTAATTTTTTAATCATACCAACGTCACTAAATTTTATTTGAT
AATGTAAAACAATCCAATATTACTTAAATATCATGAAATAAACTATTTCTATAACCAAA
```

FIG. 2

```
TTACTAAATTTATCCAATAAGAAAAAAGTTATTTAGAAGACATAAAATAAATTTTGTAA
TACTTAAATAAATTTGAAATAAAAAAAGTGAAGTCGAGTGACTTTTTTTTAATCATAAA
AAAATAAATTATTAACTTTAAACTAATAAAACATTAATATAATTTCATGAATGAAATCT
AGTACTTACCTCTTATATAAAAAAGAAAAAGTGTTTCTAATATATACTCAATTTAAATA
AAATATTTTCAATCAAATTTAGATAACAAATACTTATCAATATGAGGTCAATAACAATA
AAAAAATAATGTAAAAAAAAGGAGCAATACATAATATAAGAAAAAGATTAAAGTGCG
ATTATCAACGAGTATTATACCCTAATTTGCTAATATTTAAACTCTTATATTTAAGGTTA
TGTTCACAATATACTTAAAAAGCGCTATATTAGAGCATATATTAATTAATAAAAAGAA
AATGCTAAATGATCAAAAAAATTAGATAGAAATTAAGAAAATTATAATATTTTTTTAT
TTTAAAATAAATTGATATATTCTTTATTTTTAGTTAAAATGTATTAAAGTTAAAAGAA
TAAAAATATTTAAAAAATAAAATAACATAAATAAAATATCATTCTAATTAAATTCAGA
CCAAATTTTTTCCCCAGATTTTGGCCAATACCTAAAATAAAATTAAGTTATTTTAGTA
TATTTTTTTACATTGACCTACATTTTTCTAGTTTTTTCTAAAGGAGCGTGTAAGCGTCA
ACCTCATTCTCCTAATTTTCCCCACCACATAAATAAAAAGAAACGGTAGCTTTGCGTG
TTGTTTTGCTACACTACACCTCATTATTACACGTGTCATCATATAATTGGCTAACCCTA
TGAGGCGGTTTCGTCTAGAGTCGGCCATGCCATCTATAAAAGGAACCTTTCTGCACCTC
ATTTTTTCATCTTCTATCTGACTTCTATTATAATTTCTCTCAATTGCCTTTAAATTTCT
CTTTCAAGGTTAGAAATCTTCTCTATTTTTGGTTTTTGTCTGTTTAGATTCTCGAATT
AGCTAAGCAGGTGCTGTTAAAGCCCTAAAATTTGAGTTTTTTTCCGTTGTTTTGATGA
AAAAGCCCCTAATTTGAGTTTTTTTCCGTCGATTTGATGCCAAAGGTTTAAAATTAGAG
TTTTTTCGTCGGTTTGATTCTAAAGGCCCAAAATGTGGGGTTTTCCGGGTGATTTGATG
ATAATGCCCTAGAATTTGAGTTTTTTTATGGTGGTTTGATGAAAAAGGTCTTGAATTTG
ATTTTTTTTTCCGGTTGATTTGATGAAAAAGCCCTAGAATTTGTGATTTTTCGTCGGT
TTGATTCTAAAGCCCTAAAATTTGAGGTTTTCCGGTTGTTTTGATGAAAAAGCCCTAAA
ATTTGAGTTTTTTCCCCGTGTTTTAGATTGTTTGGTTTTAATTCTCGAATCAGTTAATC
AGGGAGTGTGAAAAGCCCTATAATTTGAGTTTTTTTCGTTGTTCCGATTGTTGTTTTTA
TGACTTTGCAGATGCAGATCTTTGTGAAAACTCTCACCGGAAAGACCATCACCCTAGAG
GTGGAACGTTCTGATACAATCGACAACGTTAAGGCTGAGATTCAGGATAAGGAAGGAAT
TCCCCCGGATCAGCAAAGGCTTATCTTCGCCGGAAAGCAGTTGGAGGACGGACGTACTC
TAGCTGATTACAACATCCAGAAGGAGTCTACCCTCCATTTGGTTCTCCGTCTACGTGGT
GGTATGCAGATCTTCGTTAAGACTCTTACGGGTAAGACGATTACCCTTGAGGTCGAAAG
CTCGGACACCATTGACAACGTTAAGGCTAAGATCCAGGATAAGGAAGGCATTCCACCAG
 ACCAGCAGAGGTTGATCTTTGCAGGAAAGCAGTTGGAAGATGGCCGCACCCTAGCCGAC
TACAACATCCAGAAGGAGTCTACCCTACATTTGGTGCTCCGTCTCCGTGGTGGTATGCA
GATCTTCGTTAAGACTCTTACCGGAAAGACCATCACTTTGGAGGTGGAAAGCTCCGACA
CCATTGACAACGTGAAGGCTAAGATCCAGGATAAGGAAGGAATTCCCCCAGACCAGCAG
AGGTTGATCTTCGCTGGTAAGCAATTGGAGGACGGCCGCACCCTAGCTGACTACAACAT
CCAGAAGGAGTCTACCCTCCATCTTGTCCTCCGTCTCCGTGGTGGTATGCAGATTTTTG
TTAAGACCCTCACCGGAAAGACCATCACTTTGGAGGTTGAAAGCTCCGACACCATTGAT
AATGTCAAGGCTAAGATCCAGGACAAGGAGGGAATTCCCCCAGACCAACAAAGGTTGAT
CTTCGCTGGAAAGCAATTGGAGGATGGCCGCACCCTAGCTGACTACAACATCCAGAAGG
AGTCCACCCTTCACCTTGTCCTCCGTCTCCGTGGTGGCATGCAGATTTTTGTTAAGACC
CTAACCGGGAAGACCATCACCCTGGAGGTTGAGAGCTCCGACACCATCGACAATGTCAA
```

FIG. 2 (cont)

```
GGCCAAGATCCAAGATAAGGAGGGTATTCCCCCAGACCAGCAGAGGTTGATCTTCGCTG
GTAAACAGCTTGAGGATGGCCGCACTCTTGCGGACTACAACATTCAGAAGGAGTCCACC
CTTCACTTGGTGCTGAGGCTGAGGGGAGGAATGCAGATCTTTGTGAAGACCTTAACCGG
GAAGACCATCACCTTGGAGGTGGAGAGTTCTGACACCATCGACAATGTGAAAGCTAAAA
TTCAGGACAAGGAGGGGATCCCACCAGACCAGCAGAGGCTGATCTTTGCTGGTAAGCAG
CTTGAAGATGGACGCACCCTTGCTGACTACAATATCCAGAAGGAGTCTACTCTGCACCT
TGTCCTCCGTCTCCGTGGTGGTTTTTAAGTTGCCTATTGTTGGTTGTCGTGTTGTCTGG
CTGTGTCTGTTGCCCATTGTGGTGGTTATGTGTTTGCATCATGGTCTAAAAGGATCATC
AATGTTTTTTCGCTTTCTGTTCCTTTCTGTTTCTCATTTGTGAATAATAATGGTGTCTT
TATGAACATCCAGTTTCTGGTTTCTTTTCTGATTGCAGTTTGAGTATTTGTTTTTGCTT
TTGCTTCCGTCTACTACACCACTTTGCAATTACTGTATCACTCATGCATTGTTGATATA
CTTTAGCCTTCGATCCATCTTCTGTTTGATGATTCAAATGGTATTTATTTAACTCATAC
CCAAGTGAAGCATAAAGTTAGAGGAGAGTTCATGTTCCATTACCTGTTTGTTTCATGAG
CAACTCATCTTAATAAACATAAGAAAAACCATAATGCAATCTGTGTAGCTGATAGACTT
TGATGACAGACGGACTCATAAGTAACAAGAGGAAACATGATAAACATGTACGGAAGTCC
TCCAACAATGACTATAATCACATGTTTTGTAGATTAGCAATGGTACATGTCAAATGAT
CTTGGATTTTAAGGAAAGGAGCTTGTGAATCAAAACATCTGAATTTGGACCTAGAGTCT
TGAGGTGATCGTACTTTGGATGGAGAGACCATGAATAAGAATGTATGAATCTGGAACTG
AGAACTAAATGGAAGACACACTGATCCAACAGATTGACCTTGTGACATTAATCACAGAA
GGTAACACGGTGACAACCAAGAACGGAGAGCTGCAAAGAATATTGTCTTAACCAACGGA
TCTTTACTGGTTTAACTGTTGTGATGTCTTTTATAGGTGGCTTTTGGATTGTTCTTTGC
TCTATCCTTTTATGTAACTTTCAAGAACCAACCAAATGAAGGTGTTCTAGATAGATATA
CATGGCATGTGAGAAGGGATCCTGAAGTTCAGATGATGGTTCATTCTAATGTGTTCCCT
TGAAGCAGTTTTCCCTTGTCTGATTTTGCCGTTCTACATGATTGAATGCTCATTTACTC
AAATAGTAGTTGCATTTTTGTTGCAGAACACGTCATTGGTCACGGTTTCGACTTTGTCT
GAGGGGCACTCGAGTTGTTGCGCTGTGTGCGTCAGTCCATTGCTCTTTAAAGAGTATTT
ATCTTGCTAGTAGAGGTTTGTTTGATATGTTTAACTTATTGTGGTAGGATTTTGCTTAT
GTGAACTCAAAATTTATCACATGCTCCTCCTTTGCATCAAATACGGAAAGGTAATGTAT
AGAAGCTT
```

FIG. 2 (cont)

```
AAGCTTATAAGATTACAAACAAAAAATCAAATACAAAGTAGAATTCTAATAAAAAGGGT
AGGAAAATCGATACAAATAAAATTATTAAAAATGAATAAGGCAACAATGAAAAAAAAAT
AAAGGTAATGAAAATCACACCAAACCTTTGTTATATAAAGAAAAAAGACAATTTTCATC
TTACAAAAAAGCAACTTCAATATACACCAAGTTGCATTAATGCTTAATGCTTGGACAGT
TGAGTTAATATTTAAGTTAAAGACAATTATTATTAAAAAACTAAAATAAGAGAGGTAAA
CATAATATATTATAAATTACCATGAAAGTAAAGTATTAGGAAATTAAACTTGAAGGGTA
GTTTGTACAATTATCTCTTTTACCTTTTGGTTATAATAATTGTAGAAAAATTAATTACT
TGAATGACTTTATAAAGAAAATTCATTAAATTGAGTGGCTTTATTGATACACACAAGT
TGATTGACTTTCTCAGATGGTAAGTGAAAAGTGCAGTGTACTATGTCTTGCATCTGCTT
AGGCTCGTTAAATAATAGAGATATTACTTAGTTGTGAGATTAGGGAGTTAATCTCATTG
TTGTGGTGTAAACTTTGCTTTACTTTTGCTTGAGAAGATTAGTAAAAACAGTTTGAAAA
TTCTTGTGAGATAGGTCATGATTTTACTTTCTTGAGCAAGGAGATTTTCACATAAAAAT
TTTGTGTCTATTTTATATTGTGATATTTACTTTATGCATTATTATTCTGCTGAGGGACA
TGATCCCGTGGTCACTTATGGACGCATACATACCAACAAATTTGTATATCTCAAAGTTA
TCGACGTCGTTGCTTTATCATCACAATTCACAACTTCTTTACTTAAAATCCGTGCCCAC
CTTGAATGGATATGCATTTTTCTAACTTTTAAAAGACACCACTTGCAACAAAAAAAGAA
TCTTTCATTTTTTAAAAAAATTATTAAATACAATATAATATAAAGTAGGCCCATAAAAA
TATCTTAATCAAGTAAATTCAAATTGGGGTAGTTGACAAAAAAGAAAAAAAATAGCAAA
CAAAAGCAAGTGTCAAGTGGATGCATAACAGTTCCCCTAGTTTTGAAAGAAGAGGTCAA
TTATGCCGCTCTTAACGTAACGCTCCACGAAGAAGCCGTTTGCACCTAAAACATCTACT
AGCCCACAGTAACGTATGGGAAAGAATTTATTCGCATCGGATAGTTTATATTAAACTAA
TATAATCTTTTATTATTATGTGATTTAACAAAGTAAAATACATGTTAATTAATTAAAAT
TAAGTAAAATGAACTGTAAATTTAAATATATGGCGTGCATGTATTGAATTGACGTATAC
ACCTGGTCCGGATAAGTTTTACCCTAATATAAATAGTAATCGTCAAAGTAAGCGGTGTA
GTATATACGATCTTTAGTACATGGTGTAGTAAATACGATTTTGAATAAAAAACATTTC
TTTCTAAATAACTATTTAACATAAATTTAAAATGATCAAACTTTAATATAAATATTAGA
TGTCAAATAAAAGAATTAAAAAGAAAATATGAATAGTAGATTTAGACTATTTGTTGAGT
CTCATTTATCGAAAATATTTTTTTTTAGGTATTCTATTTTTTCTAAACGTCATTTTGA
GGAACTACATACCATGGATATAAAAAAGGGACAAAAATAATACAATTTTTGTTCAACTA
ATCTTTTTTTTTTTTTCGCTTTTAAAAAAGAGGAGAGTGATGGTTAATAATTAAATA
ATGAAAAGAAGGAAAGAAAATTTTCGAATAAAAATGTCAAAAGAGAAAAAAAGAGAGG
GAGTAATCATTGATCAACTTTATACAGAATCAAGTACCCCAATTTGATTTTTCATGGAT
ATCAAAATTTACAAGAATTTATTAAAATATAGATATCGGGTAAATTTATTAACAAGATT
TGAACATATAAATAAAATTATGTAATATTTCAACTCTAAATAAACTAATATTTGAAAT
CTCAAATTTATGATTTTAAATTTACTTTATATCCAAGACAATTTCAGCTTAAAAAGGT
TTATTAATATTTACATTAGTTTTGTTGATGAGGATGACAAGAATTTGGTCATCAACTAC
ATATACCCAAATTGAATAGTAAGCAACTTAATGTTTTTCATAATGATAATATGACAGAC
ACAAAAAAAAAACCATTCATTATTCACATAGATTGATTTTATATGCAATATAATAAT
AATAATAATAATAATAATAATAATAATAATAATATATATATATATATATTTCTTAT
AAAGCAAGAGGTCAATTTAATTTTTTTAATCATACCAACGTCACTAAATTTTATTTGAT
AATGTAAAACAATCCAATATTACTTAAATATCATGAAATAAACTATTTCTATAACCAAA
TTACTAAATTTATCCAATAAGAAAAAAGTTATTTAGAAGACATAAAATAAATTTTGTAA
```

FIG. 3

```
TACTTAAATAAATTTGAAATAAAAAAAGTGAAGTCGAGTGACTTTTTTTTAATCATAAA
AAAATAAATTATTAACTTTAAACTAATAAAACATTAATATAATTTCATGAATGAAATCT
AGTACTTACCTCTTATATAAAAAGAAAAAGTGTTTCTAATATATACTCAATTTAAATA
AAATATTTTCAATCAAATTTAGATAACAAATACTTATCAATATGAGGTCAATAACAATA
AAAAAATAATGTAAAAAAAAGGAGCAATACATAATATAAGAAAAAGATTAAAGTGCG
ATTATCAACGAGTATTATACCCTAATTTGCTAATATTTAAACTCTTATATTTAAGGTTA
TGTTCACAATATACTTAAAAAGCGCTATATTAGAGCATATATTAATTAATAAAAAAGAA
AATGCTAAATGATCAAAAAATTAGATAGAAAATTAAGAAAATTATAATATTTTTTTAT
TTTAAAATAAATTGATATATTCTTTATTTTTAGTTAAAATGTATTAAAGTTAAAAGAA
TAAAAATATTTTAAAAAATAAAATAACATAAATAAAATATCATTCTAATTAAATTCAGA
CCAAATTTTTTCCCCAGATTTTGGCCAATACCTAAAATAAAATTAAGTTATTTTAGTA
TATTTTTTACATTGACCTACATTTTTCTAGTTTTTTCTAAAGGAGCGTGTAAGCGTCA
ACCTCATTCTCCTAATTTTCCCCACCACATAAATAAAAAGAAACGGTAGCTTTTGCGTG
TTGTTTGCTACACTACACCTCATTATTACACGTGTCATCATATAATTGGCTAACCCTA
TGAGGCGGTTTCGTCTAGAGTCGGCCATGCCATCTATAAAAGGAACCTTTCTGCACCTC
ATTTTTTCATCTTCTATCTGACTTCTATTATAATTTCTCTCAATTGCCTTTAAATTTCT
CTTTCAAGGTTAGAAATCTTCTCTATTTTTGGTTTTTGTCTGTTTAGATTCTCGAATT
AGCTAAGCAGGTGCTGTTAAAGCCCTAAAATTTGAGTTTTTTTCCGTTGTTTTGATGA
AAAAGCCCCTAATTTGAGTTTTTTTCCGTCGATTTGATGCCAAAGGTTTAAAATTAGAG
TTTTTTCGTCGGTTTGATTCTAAAGGCCCAAAATGTGGGGTTTTCCGGGTGATTTGATG
ATAATGCCCTAGAATTTGAGTTTTTTTATGGTGGTTTGATGAAAAAGGTCTTGAATTTG
ATTTTTTTTTTCCGGTTGATTTGATGAAAAAGCCCTAGAATTTGTGATTTTTCGTCGGT
TTGATTCTAAAGCCCTAAAATTTGAGGTTTTCCGGTTGTTTTGATGAAAAAGCCCTAAA
ATTTGAGTTTTTTCCCCGTGTTTTAGATTGTTTGGTTTAATTCTCGAATCAGTTAATC
AGGGAGTGTGAAAAGCCCTATAATTTGAGTTTTTTTCGTTGTTCCGATTGTTGTTTTTA
TGACTTTGCAGATGCAGATCTTTGTGAAAACTCTCACCGGAAAGACCATCACCCTAGAG
GTGGAACGTTCTGATACAATCGACAACGTTAAGGCTGAGATTCAGGATAAGGAAGGAAT
TCCCCCGGATCAGCAAAGGCTTATCTTCGCCGGAAAGCAGTTGGAGGACGGACGTACTC
TAGCTGATTACAACATCCAGAAGGAGTCTACCCTCCATTTGGTTCTCCGTCTACGTGGT
GGT
```

FIG. 3 (cont)

```
ACTTACCTCTTATATAAAAAAGAAAAAGTGTTTCTAATATATACTCAATTTAAATAAAA
TATTTTCAATCAAATTTAGATAACAAATACTTATCAATATGAGGTCAATAACAATAAAA
AAATAATGTAAAAAAAAGGAGCAATACATAATATAAGAAAAAGATTAAAGTGCGATT
ATCAACGAGTATTATACCCTAATTTGCTAATATTTAAACTCTTATATTTAAGGTTATGT
TCACAATATACTTAAAAAGCGCTATATTAGAGCATATATTAATTAATAAAAAGAAAAT
GCTAAATGATCAAAAAATTAGATAGAAAATTAAGAAAATTATAATATTTTTTTATTTT
AAAATAAATTGATATATTCTTTATTTTTAGTTAAAATGTATTAAAGTTAAAAGAATAA
AAATATTTTAAAAAATAAAATAACATAAATAAAATATCATTCTAATTAAATTCAGACCA
AATTTTTTCCCCAGATTTTGGCCAATACCTAAAATAAAATTAAGTTATTTTAGTATAT
TTTTTTACATTGACCTACATTTTTCTAGTTTTTTCTAAAGGAGCGTGTAAGCGTCAACC
TCATTCTCCTAATTTTCCCCACCACATAAATAAAAAGAAACGGTAGCTTTTGCGTGTTG
TTTTGCTACACTACACCTCATTATTACACGTGTCATCATATAATTGGCTAACCCTATGA
GGCGGTTTCGTCTAGAGTCGGCCATGCCATCTATAAAAGGAACCTTTCTGCACCTCATT
TTTTCATCTTCTATCTGACTTCTATTATAATTTCTCTCAATTGCCTTTAAATTTCTCTT
TCAAGGTTAGAAATCTTCTCTATTTTTGGTTTTGTCTGTTTAGATTCTCGAATTAGC
TAAGCAGGTGCTGTTAAAGCCCTAAAATTTGAGTTTTTTTCCGTTGTTTTGATGAAAA
AGCCCCTAATTTGAGTTTTTTTCCGTCGATTTGATGCCAAAGGTTTAAAATTAGAGTTT
TTTCGTCGGTTTGATTCTAAAGGCCCAAAATGTGGGGTTTTCCGGGTGATTTGATGATA
ATGCCCTAGAATTTGAGTTTTTTTATGGTGGTTTGATGAAAAAGGTCTTGAATTTGATT
TTTTTTTTCCGGTTGATTTGATGAAAAAGCCCTAGAATTTGTGATTTTTCGTCGGTTTG
ATTCTAAAGCCCTAAAATTTGAGGTTTTCCGGTTGTTTTGATGAAAAAGCCCTAAAATT
TGAGTTTTTTCCCCGTGTTTTAGATTGTTTGGTTTTAATTCTCGAATCAGTTAATCAGG
GAGTGTGAAAAGCCCTATAATTTGAGTTTTTTTCGTTGTTCCGATTGTTGTTTTATGA
CTTTGCAGATGCAGATCTTTGTGAAAACTCTCACCGGAAAGACCATCACCCTAGAGGTG
GAACGTTCTGATACAATCGACAACGTTAAGGCTGAGATTCAGGATAAGGAAGGAATTCC
CCCGGATCAGCAAAGGCTTATCTTCGCCGGAAAGCAGTTGGAGGACGGACGTACTCTAG
CTGATTACAACATCCAGAAGGAGTCTACCCTCCATTTGGTTCTCCGTCTACGTGGTGGT
GGATCCCCGGGTGGTCAGTCCCTTATGTTACGTCCTGTAGAAACCCCAACCCGTGAAAT
CAAAAAACTCGACGGCCTGTGGGCATTCAGTCTGGATCGCGAAACTGTGGAATTGATC
AGCGTTGGTGGGAAGCGCGTTACAAGAAGCCGGGCAATTGCTGTGCCAGGCAGTTTT
AACGATCAGTTCGCCGATGCAGATATTCGTAATTATGCGGGCAACGTCTGGTATCAGCG
CGAAGTCTTTATACCGAAAGGTTGGGCAGGCCAGCGTATCGTGCTGCGTTTCGATGCGG
TCACTCATTACGGCAAAGTGTGGGTCAATAATCAGGAAGTGATGGAGCATCAGGGCGGC
TATACGCCATTTGAAGCCGATGTCACGCCGTATGTTATTGCCGGGAAAGTGTACGTAT
CACCGTTTGTGTGAACAACGAACTGAACTGGCAGACTATCCCGCCGGGAATGGTGATTA
CCGACGAAAACGGCAAGAAAAGCAGTCTTACTTCCATGATTTCTTTAACTAT
```

FIG. 4

```
GCCGGAATCCATCGCAGCGTAATGCTCTACACCACGCCGAACACCTGGGTGGACGATAT
CACCGTGGTGACGCATGTCGCGCAAGACTGTAACCACGCGTCTGTTGACTGGCAGGTGG
TGGCCAATGGTGATGTCAGCGTTGAACTGCGTGATGCGGATCAACAGGTGGTTGCAACT
GGACAAGGCACTAGCGGGACTTTGCAAGTGGTGAATCCGCACCTCTGGCAACCGGGTGA
AGGTTATCTCTATGAACTGTGCGTCACAGCCAAAAGCCAGACAGAGTGTGATATCTACC
CGCTTCGCGTCGGCATCCGGTCAGTGGCAGTGAAGGGCGAACAGTTCCTGATTAACCAC
AAACCGTTCTACTTTACTGGCTTTGGTCGTCATGAAGATGCGGACTTGCGTGGCAAAGG
ATTCGATAACGTGCTGATGGTGCACGACCACGCATTAATGGACTGGATTGGGGCCAACT
CCTACCGTACCTCGCATTACCCTTACGCTGAAGAGATGCTCGACTGGGCAGATGAACAT
GGCATCGTGGTGATTGATGAAACTGCTGCTGTCGGCTTTAACCTCTCTTTAGGCATTGG
TTTCGAAGCGGGCAACAAGCCGAAAGAACTGTACAGCGAAGAGGCAGTCAACGGGGAAA
CTCAGCAAGCGCACTTACAGGCGATTAAAGAGCTGATAGCGCGTGACAAAAACCACCCA
AGCGTGGTGATGTGGAGTATTGCCAACGAACCGGATACCCGTCCGCAAGGTGCACGGGA
ATATTTCGCGCCACTGGCGGAAGCAACGCGTAAACTCGACCCGACGCGTCCGATCACCT
GCGTCAATGTAATGTTCTGCGACGCTCACACCGATACCATCAGCGATCTCTTTGATGTG
CTGTGCCTGAACCGTTATTACGGATGGTATGTCCAAAGCGGCGATTTGGAAACGGCAGA
GAAGGTACTGGAAAAGAACTTCTGGCCTGGCAGGAGAAACTGCATCAGCCGATTATCA
TCACCGAATACGGCGTGGATACGTTAGCCGGGCTGCACTCAATGTACACCGACATGTGG
AGTGAAGAGTATCAGTGTGCATGGCTGGATATGTATCACCGCGTCTTTGATCGCGTCAG
CGCCGTCGTCGGTGAACAGGTATGGAATTTCGCCGATTTTGCGACCTCGCAAGGCATAT
TGCGCGTTGGCGGTAACAAGAAAGGGATCTTCACTCGCGACCGCAAACCGAAGTCGGCG
GCTTTTCTGCTGCAAAAACGCTGGACTGGCATGAACTTCGGTGAAAAACCGCAGCAGGG
AGGCAAACAATGATATCATACAACTCTCCTGGCGCACCATCGTCGGCTACAGCCTCGGG
AATTGCTACCGAGCTCGAATTTCCCCGATCGTTCAAACATTTGGCAATAAAGTTTCTTA
AGATTGAATCCTGTTGCCGGTCTTGCGATGATTATCATATAATTTCTGTTGAATTACGT
TAAGCATGTAATAATTAACATGTAATGCATGACGTTATTTATGAGATGGGTTTTTATGA
TTAGAGTCCCGCAATTATACATTTAATACGCGATAGAAAACAAAATATAGCGCGCAAAC
TAGGATAAATTATCGCGCGCGGTGTCATCTATGTTACTAGATCGGGAATTGATCCCCGG
GTACC
```

FIG. 4 (cont)

```
                       SEQUENCE LISTING

<160> NUMBER OF SEQ ID NOS: 4

<210> SEQ ID NO 1
<211> LENGTH: 1593
<212> TYPE: DNA
<213> ORGANISM: Solanum bulbocastanum

<400> SEQUENCE: 1
acttacctct tatataaaaa agaaaaagtg tttctaatat atactcaatt taaataaaat      60
attttcaatc aaatttagat aacaaatact tatcaatatg aggtcaataa caataaaaaa     120
ataatgtaaa aaaaaaggag caatacataa tataagaaaa aagattaaag tgcgattatc     180
aacgagtatt atacccctaat ttgctaatat ttaaactctt atatttaagg ttatgttcac    240
aatatactta aaaagcgcta tattagagca tatattaatt aataaaaaag aaaatgctaa     300
atgatcaaaa aaattagata gaaattaag aaaattataa tatttttta ttttaaaata       360 aattgatata ttctttattt tttagttaaa atgtattaaa gttaaaagaa taaaaatatt     420
ttaaaaaata aaataacata aataaaatat cattctaatt aaattcagac caaatttttt    480
ccccagattt tggccaatac ctaaaataaa attaagttat ttttagtata ttttttttaca    540 ttgacctaca tttttctagt ttttctaaa ggagcgtgta agcgtcaacc tcattctcct      600
aattttcccc accacataaa taaaagaaa cggtagcttt tgcgtgttgt tttgctacac      660
tacacctcat tattacacgt gtcatcatat aattggctaa ccctatgagg cggtttcgtc     720
tagagtcggc catgccatct ataaaggaa cctttctgca cctcattttt tcatcttcta      780
tctgacttct attataattt ctctcaattg cctttaaatt tctctttcaa ggttagaaat     840
cttctctatt ttttggtttt tgtctgttta gattctcgaa ttagctaagc aggtgctgtt     900
aaagccctaa aatttgagtt ttttttccgt tgttttgatg aaaaagcccc taatttgagt     960 tttttccgt cgatttgatg ccaaaggttt aaaattagag ttttttcgtc ggtttgattc     1020
taaaggccca aaatgtgggg ttttccgggt gatttgatga taatgcccta gaatttgagt    1080 tttttatgg tggtttgatg aaaaaggtct tgaatttgat tttttttttc cggttgattt     1140
gatgaaaaag ccctagaatt tgtgattttt cgtcggtttg attctaaagc cctaaaattt    1200
```

```
gaggttttcc ggttgttttg atgaaaaagc cctaaaattt gagttttttc cccgtgtttt      1260
agattgtttg gttttaattc tcgaatcagt taatcaggga gtgtgaaaag ccctataatt      1320 tgagttttt  tcgttgttcc gattgttgtt tttatgactt tgcagatgca gatctttgtg      1380
aaaactctca ccggaaagac catcacccta gaggtggaac gttctgatac aatcgacaac      1440
gttaaggctg agattcagga taaggaagga attccccggg atcagcaaag gcttatcttc      1500
gccggaaagc agtggagga  cggacgtact ctagctgatt acaacatcca gaaggagtct      1560
accctccatt tggttctccg tctacgtggt ggt                                   1593

<210> SEQ ID NO 2
<211> LENGTH: 6616
<212> TYPE: DNA
<213> ORGANISM: Solanum bulbocastanum

<400> SEQUENCE: 2
aagcttataa gattacaaac aaaaaatcaa atacaaagta gaattctaat aaaaagggta        60
ggaaaatcga tacaaataaa attattaaaa atgaataagg caacaatgaa aaaaaaataa       120
aggtaatgaa atcacacca  aacctttgtt atataaagaa aaaagacaat tttcatctta       180
caaaaaagca acttcaatat acaccaagtt gcattaatgc ttaatgcttg dacagttgag       240
ttaatattta agttaaagac aattattatt aaaaaactaa ataagagag  gtaaacataa       300 tatattataa attaccatga aagtaaagta ttaggaaatt aaacttgaag ggtagttgt        360 acaattatct cttttacctt ttggttataa taattgtaga aaaattaatt acttgaatga       420
ctttataaaa gaaaattcat taaattgagt ggctttattg atacacacaa gttgattgac       480
tttctcagat ggtaagtgaa aagtgcagtg tactatgtct tgcatctgct taggctcgtt       540 aaataatgaga gatattactt agttgtgaga ttagggagtt aatctcattg ttgtggtgta      600
aactttgctt tacttttgct tgagaagatt agtaaaaaca gtttgaaaat tcttgtgaga       660
taggtcatga ttttactttc ttgagcaagg agattttcac ataaaaattt tgtgtctatt       720
ttatattgtg atatttactt tatgcattat tattctgctg agggacatga tcccgtggtc       780
acttatggac gcatacatac caacaaattt gtatatctca aagttatcga cgtcgttgct       840
ttatcatcac aattcacaac ttctttactt aaaatccgtg cccaccttga atggatatgc       900
attttttcta acttttaaaag acaccacttg caacaaaaaa gaatctttc atttttaaa        960 aaaattatta aatacaatat aatataaagt aggcccataa aaatatctta atcaagtaaa      1020
ttcaaattgg ggtagttgac aaaaaagaaa aaaaatagca aacaaagca  agtgtcaagt      1080 ggatgcataa cagttcccct agttttgaaa aagaggtca  attatgccgc tcttaacgta      1140
acgctccacg aagaagccgt ttgcacctaa acatctact  agcccacagt aacgtatggg      1200
aaagaattta ttcgcatcgg atagtttata ttaaactaat ataatctttt attattatgt      1260
gatttaacaa agtaaaatac atgttaatta attaaaatta gtaaaatga  actgtaaatt      1320 taaatatatg gcgtgcatgt attgaattga cgtatacacc tggtccggat aagttttacc      1380
ctaatataaa tagtaatcgt caaagtaagc ggtgtagtat atacgatctt tagtacatgg      1440
tgtagtaaat acgattttg  aataaaaaac atttctttct aaataactat ttaacataaa      1500
tttaaaatga tcaaacttta atataaatat tagatgtcaa ataaaagaat taaaagaaa       1560 atatgaatag tagatttaga ctatttgttg agtctcattt atcgaaaata ttttttttt       1620 aggtattcta ttttttctaa acgtcatttt gaggaactac ataccatgga tataaaaag       1680 ggacaaaaat aatacaattt ttgttcaact aatctttttt ttttttttc gcttttaaaa       1740
```

```
aagaggagag tgatggttaa taattaaata atgaaaaaga aggaaagaaa attttcgaat    1800
aaaaatgtca aagagaaaa aaagagaggg agtaatcatt gatcaacttt atacagaatc    1860
aagtacccca atttgatttt tcatggatat caaaatttac aagaatttat taaaatatag   1920
atatcgggta aatttattaa caagatttga acatataaat aaaaattatg taatatttca   1980
actctaaata aactaatatt tgaaatctca aatttatgat ttttaaattt actttatatc   2040
caagacaatt tcagcttaaa aaggtttatt aatatttaca ttagttttgt tgatgaggat   2100
gacaagaatt tggtcatcaa ctacatatac ccaaattgaa tagtaagcaa cttaatgttt   2160
ttcataatga taatatgaca gacacaaaaa aaaaaaccat tcattattca catagattga   2220
tttttatatg caatataata ataataataa taataataat aataataata ataataatat   2280
atatatatat atatttctta taaagcaaga ggtcaattta atttttttaa tcataccaac   2340
gtcactaaat tttatttgat aatgtaaaac aatccaatat tacttaaata tcatgaaata   2400
aactatttct ataaccaaat tactaaattt atccaataag aaaaaagtta tttagaagac   2460
ataaaataaa ttttgtaata cttaaataaa tttgaaataa aaaaagtgaa gtcgagtgac   2520
ttttttttaa tcataaaaaa ataaattatt aactttaaac taataaaaca ttaatataat   2580
ttcatgaatg aaatctagta cttacctctt atataaaaaa gaaaaagtgt ttctaatata   2640
tactcaattt aaataaaata ttttcaatca aatttagata acaaatactt atcaatatga   2700
ggtcaataac aataaaaaaa taatgtaaaa aaaaaggagc aatacataat ataagaaaaa   2760
agattaaagt gcgattatca acgagtatta taccctaatt tgctaatatt taaactctta   2820
tatttaaggt tatgttcaca atatacttaa aaagcgctat attagagcat atattaatta   2880
ataaaaaaga aaatgctaaa tgatcaaaaa aattagatag aaaattaaga aaattataat   2940 attttttttat tttaaaataa attgatatat tctttatttt ttagttaaaa tgtattaaag   3000 ttaaagaat aaaaatattt taaaaataa aataacataa ataaaatatc attctaatta   3060
aattcagacc aaatttttc cccagatttt ggccaatacc taaaataaaa ttaagttatt    3120
tttagtatat tttttacat tgacctacat ttttctagtt ttttctaaag gagcgtgtaa    3180
gcgtcaacct cattctccta attttcccca ccacataaat aaaaagaaac ggtagctttt   3240
gcgtgttgtt ttgctacact acacctcatt attacacgtg tcatcatata attggctaac   3300
cctatgaggc ggtttcgtct agagtcggcc atgccatcta taaaggaac cttctctgcac   3360 ctcattttt catcttctat ctgacttcta ttataatttc tctcaattgc ctttaaattt    3420
ctctttcaag gttagaaatc ttctctattt tttggttttt gtctgtttag attctcgaat   3480
tagctaagca ggtgctgtta aagccctaaa atttgagttt ttttccgtt gttttgatga    3540 aaaagccct aatttgagtt ttttccgtc gatttgatgc caaggttta aaattagagt     3600 tttttcgtcg gtttgattct aaaggcccaa aatgtggggt ttccgggtg atttgatgat   3660 aatgccctag aatttgagtt ttttatggt ggtttgatga aaaaggtctt gaatttgatt   3720
ttttttttcc ggttgatttg atgaaaaagc cctagaattt gtgattttc gtcggtttga    3780 ttctaaagcc ctaaaatttg aggttttccg gttgttttga tgaaaagcc ctaaatttg    3840 agtttttcc ccgtgtttta gattgtttgg ttttaattct cgaatcagtt aatcaggag    3900 tgtgaaaagc cctataattt gagttttttt cgttgttccg attgttgttt ttatgacttt   3960
gcagatgcag atctttgtga aaactctcac cggaaagacc atcacctag aggtggaacg    4020 ttctgataca atcgacaacg ttaaggctga gattcaggat aaggaaggaa ttccccgga    4080
```

```
tcagcaaagg cttatcttcg ccggaaagca gttggaggac ggacgtactc tagctgatta      4140
caacatccag aaggagtcta ccctccattt ggttctccgt ctacgtggtg gtatgcagat      4200
cttcgttaag actcttacgg gtaagacgat tacccttgag gtcgaaagct cggacaccat      4260
tgacaacgtt aaggctaaga tccaggataa ggaaggcatt ccaccagacc agcagaggtt      4320
gatctttgca ggaaagcagt tggaagatgg ccgcacccta gccgactaca acatccagaa      4380
ggagtctacc ctacatttgg tgctccgtct ccgtggtggt atgcagatct tcgttaagac      4440
tcttaccgga aagaccatca ctttggaggt ggaaagctcc gacaccattg acaacgtgaa      4500
ggctaagatc caggataagg aaggaattcc cccagaccag cagaggttga tcttcgctgg      4560
taagcaattg gaggacggcc gcaccctagc tgactacaac atccagaagg agtctaccct      4620
ccatcttgtc ctccgtctcc gtggtggtat gcagattttt gttaagccc tcaccggaaa      4680 gaccatcact ttggaggttg aaagctccga caccattgat aatgtcaagg ctaagatcca      4740
ggacaaggag ggaattcccc cagaccaaca aaggttgatc ttcgctggaa agcaattgga      4800
ggatggccgc accctagctg actacaacat ccagaaggag tccacccttc accttgtcct      4860
ccgtctccgt ggtggcatgc agattttgt taagaccccta accgggaaga ccatcaccct      4920
ggaggttgag agctccgaca ccatcgacaa tgtcaaggcc aagatccaag ataaggaggg      4980
tattccccca gaccagcaga ggttgatctt cgctggtaaa cagcttgagg atggccgcac      5040
tcttgcggac tacaacattc agaaggagtc cacccttcac ttggtgctga ggctgagggg      5100
aggaatgcag atctttgtga agaccttaac cgggaagacc atcaccttgg aggtggagag      5160
ttctgacacc atcgacaatg tgaaagctaa aattcaggac aaggagggga tcccaccaga      5220
ccagcagagg ctgatctttg ctggtaagca gcttgaagat ggacgcaccc ttgctgacta      5280
caatatccag aaggagtcta ctctgcacct tgtcctccgt ctccgtggtg gtttttaagt      5340
tgcctattgt tggttgtcgt gttgtctggc tgtgtctgtt gcccattgtg gtggttatgt      5400
gtttgcatca tggtctaaaa ggatcatcaa tgttttttcg ctttctgttc ctttctgttt      5460
ctcatttgtg aataataatg gtgtctttat gaacatccag tttctggttt cttttctgat      5520
tgcagtttga gtatttgttt ttgcttttgc ttccgtctac tacaccactt tgcaattact      5580
gtatcactca tgcattgttg atatacttta gccttcgatc catcttctgt ttgatgattc      5640
aaatggtatt tatttaactc ataccccaagt gaagcataaa gttagaggag agttcatgtt      5700
ccattacctg tttgtttcat gagcaactca tcttaataaa cataagaaaa accataatgc      5760
aatctgtgta gctgatagac tttgatgaca gacggactca taagtaacaa gaggaaacat      5820
gataaacatg tacggaagtc ctccaacaat gactataatc acatgttttt gtagattagc      5880
aatggtacat gtcaaatgat cttggatttt aaggaaagga gcttgtgaat caaaacatct      5940
gaatttggac ctagagtctt gaggtgatcg tactttggat ggagagacca tgaataagaa      6000
tgtatgaatc tggaactgag aactaaatgg aagacacact gatccaacag attgaccttg      6060
tgacattaat cacagaaggt aacacggtga caaccaagaa cggagagctg caaagaatat      6120
tgtcttaacc aacggatctt tactggttta actgttgtga tgtctttat aggtggcttt      6180 tggattgttc tttgctctat cctttatgt aactttcaag aaccaaccaa atgaaggtgt      6240
tctagataga tatacatggc atgtgagaag ggatcctgaa gttcagatga tggttcattc      6300
taatgtgttc ccttgaagca gttttcccctt gtctgatttt gccgttctac atgattgaat      6360
gctcatttac tcaaatagta gttgcatttt tgttgcagaa cacgtcattg gtcacggttt      6420
cgactttgtc tgagggggcac tcgagttgtt gcgctgtgtg cgtcagtcca ttgctcttta      6480
```

<210> SEQ ID NO 3
<211> LENGTH: 4192
<212> TYPE: DNA
<213> ORGANISM: Solanum Bulbocastanum

<400> SEQUENCE: 3

| | | | | | |
|---|---|---|---|---|---|
| aagagtattt | atcttgctag | tagaggtttg | tttgatatgt | ttaacttatt | gtggtaggat | 6540 |
| tttgcttatg | tgaactcaaa | atttatcaca | tgctcctcct | ttgcatcaaa | tacggaaagg | 6600 |
| taatgtatag | aagctt | | | | | 6616 |

| | | | | | |
|---|---|---|---|---|---|
| aagcttataa | gattacaaac | aaaaaatcaa | atacaaagta | gaattctaat | aaaaagggta | 60 |
| ggaaaatcga | tacaaataaa | attattaaaa | atgaataagg | caacaatgaa | aaaaaaataa | 120 |
| aggtaatgaa | aatcacacca | aacctttgtt | atataaagaa | aaaagacaat | tttcatctta | 180 |
| caaaaagca | acttcaatat | acaccaagtt | gcattaatgc | ttaatgcttg | acagttgag | 240 |
| ttaatattta | agtaaagac | aattattatt | aaaaaactaa | aataagagag | gtaaacataa | 300 |
| tatattataa | attaccatga | aagtaaagta | ttaggaaatt | aaacttgaag | ggtagtttgt | 360 |
| acaattatct | cttttacctt | ttggttataa | taattgtaga | aaaattaatt | acttgaatga | 420 |
| ctttataaaa | gaaaattcat | taaattgagt | ggctttattg | atacacacaa | gttgattgac | 480 |
| tttctcagat | ggtaagtgaa | aagtgcagtg | tactatgtct | tgcatctgct | taggctcgtt | 540 |
| aaataataga | gatattactt | agttgtgaga | ttagggagtt | aatctcattg | ttgtggtgta | 600 |
| aacttttgctt | tacttttgct | tgagaagatt | agtaaaaaca | gtttgaaaat | tcttgtgaga | 660 |
| taggtcatga | ttttactttc | ttgagcaagg | agattttcac | ataaaaattt | tgtgtctatt | 720 |
| ttatattgtg | atatttactt | tatgcattat | tattctgctg | agggacatga | tcccgtggtc | 780 |
| acttatggac | gcatacatac | caacaaattt | gtatatctca | aagttatcga | cgtcgttgct | 840 |
| ttatcatcac | aattcacaac | ttctttactt | aaaatccgtg | cccaccttga | atggatatgc | 900 |
| attttttctaa | cttttaaaag | acaccacttg | caacaaaaaa | agaatctttc | attttttaaa | 960 |
| aaaattatta | aatacaatat | aatataaagt | aggcccataa | aaatatctta | atcaagtaaa | 1020 |
| ttcaaattgg | ggtagttgac | aaaaaagaaa | aaaaatagca | acaaaagca | agtgtcaagt | 1080 |
| ggatgcataa | cagttcccct | agttttgaaa | gaagaggtca | attatgccgc | tcttaacgta | 1140 |
| acgctccacg | aagaagccgt | ttgcacctaa | acatctact | agcccacagt | aacgtatggg | 1200 |
| aaagaattta | ttcgcatcgg | atagtttata | ttaaactaat | ataatctttt | attattatgt | 1260 |
| gatttaacaa | agtaaaatac | atgttaatta | attaaaatta | agtaaaatga | actgtaaatt | 1320 |
| taaatatatg | gcgtgcatgt | attgaattga | cgtatacacc | tggtccggat | aagttttacc | 1380 |
| ctaatataaa | tagtaatcgt | caaagtaagc | ggtgtagtat | atacgatctt | tagtacatgg | 1440 |
| tgtagtaaat | acgattttg | aataaaaaac | atttctttct | aaataactat | ttaacataaa | 1500 |
| tttaaaatga | tcaaacttta | atataaatat | tagatgtcaa | ataaaagaat | taaaagaaa | 1560 |
| atatgaatag | tagatttaga | ctatttgttg | agtctcattt | atcgaaaata | ttttttttttt | 1620 |
| aggtattcta | tttttttctaa | acgtcatttt | gaggaactac | ataccatgga | tataaaaaag | 1680 |
| ggacaaaaat | aatacaattt | ttgttcaact | aatctttttt | ttttttttttc | gcttttaaaa | 1740 |
| aagaggagag | tgatggttaa | taattaaata | atgaaaaaga | aggaaagaaa | attttcgaat | 1800 |
| aaaaatgtca | aaagagaaaa | aaagagaggg | agtaatcatt | gatcaacttt | atacagaatc | 1860 |
| aagtacccca | atttgatttt | tcatggatat | caaaatttac | aagaatttat | taaaatatag | 1920 |

-continued

| | |
|---|---|
| atatcgggta aatttattaa caagatttga acatataaat aaaaattatg taatatttca | 1980 |
| actctaaata aactaatatt tgaaatctca aatttatgat tttaaattt actttatatc | 2040 |
| caagacaatt tcagcttaaa aaggtttatt aatatttaca ttagttttgt tgatgaggat | 2100 |
| gacaagaatt tggtcatcaa ctacatatac ccaaattgaa tagtaagcaa cttaatgttt | 2160 |
| ttcataatga taatatgaca gacacaaaaa aaaaaaccat tcattattca catagattga | 2220 |
| tttttatatg caatataata ataataataa taataataat aataataata ataataatat | 2280 |
| atatatatat atatttctta taaagcaaga ggtcaatttta atttttttaa tcataccaac | 2340 |
| gtcactaaat tttatttgat aatgtaaaac aatccaatat tacttaaata tcatgaaata | 2400 |
| aactatttct ataaccaaat tactaaattt atccaataag aaaaaagtta tttagaagac | 2460 |
| ataaaataaa ttttgtaata cttaaataaa tttgaaataa aaaaagtgaa gtcgagtgac | 2520 |
| ttttttttaa tcataaaaaa ataaattatt aactttaaac taataaaaca ttaatataat | 2580 |
| ttcatgaatg aaatctagta cttacctctt atataaaaaa gaaaaagtgt ttctaatata | 2640 |
| tactcaattt aaataaaata ttttcaatca aatttagata acaaatactt atcaatatga | 2700 |
| ggtcaataac aataaaaaaa taatgtaaaa aaaaaggagc aatacataat ataagaaaaa | 2760 |
| agattaaagt gcgattatca acgagtatta taccctaatt tgctaatatt taaactctta | 2820 |
| tatttaaggt tatgttcaca atatacttaa aaagcgctat attagagcat atattaatta | 2880 |
| ataaaaaaga aaatgctaaa tgatcaaaaa aattagatag aaaattaaga aaattataat | 2940 |
| atttttttat tttaaaataa attgatatat tctttatttt ttagttaaaa tgtattaaag | 3000 |
| ttaaaagaat aaaaatattt taaaaaataa aataacataa ataaaatatc attctaatta | 3060 |
| aattcagacc aaatttttc cccagatttt ggccaatacc taaaataaaa ttaagttatt | 3120 |
| tttagtatat ttttttacat tgacctacat ttttctagtt ttttctaaag gagcgtgtaa | 3180 |
| gcgtcaacct cattctccta attttcccca ccacataaat aaaaagaaac ggtagctttt | 3240 |
| gcgtgttgtt ttgctacact acacctcatt attacacgtg tcatcatata attggctaac | 3300 |
| cctatgaggc ggtttcgtct agagtcggcc atgccatcta taaaggaac cttctgcac | 3360 |
| ctcatttttt catcttctat ctgacttcta ttataatttc tctcaattgc cttaaatttt | 3420 |
| ctctttcaag gttagaaatc ttctctattt tttggttttt gtctgtttag attctcgaat | 3480 |
| tagctaagca ggtgctgtta aagccctaaa atttgagttt ttttccgtt gttttgatga | 3540 |
| aaaagcccct aatttgagtt ttttccgtc gatttgatgc caaaggttta aaattagagt | 3600 |
| tttttcgtcg gttgattct aaaggcccaa aatgtggggt tttccgggtg atttgatgat | 3660 |
| aatgccctag aatttgagtt tttttatggt ggtttgatga aaaaggtctt gaatttgatt | 3720 |
| tttttttcc ggttgatttg atgaaaaagc cctagaattt gtgattttc gtcggtttga | 3780 |
| ttctaaagcc ctaaaatttg aggttttccg gttgttttga tgaaaaagcc ctaaaatttg | 3840 |
| agtttttcc ccgtgttta gattgtttgg ttttaattct cgaatcagtt aatcagggag | 3900 |
| tgtgaaaagc cctataattt gagttttttt cgttgttccg attgttgttt ttatgacttt | 3960 |
| gcagatgcag atctttgtga aaactctcac cggaaagacc atcaccctag aggtggaacg | 4020 |
| ttctgataca atcgacaacg ttaaggctga gattcaggat aaggaaggaa ttccccggga | 4080 |
| tcagcaaagg cttatcttcg ccggaaagca gttggaggac ggacgtactc tagctgatta | 4140 |
| caacatccag aaggagtcta ccctccattt ggttctccgt ctacgtggtg gt | 4192 |

<210> SEQ ID NO 4
<211> LENGTH: 3775

```
<212> TYPE: DNA
<213> ORGANISM: Artificial Sequence
<220> FEATURE:
<223> OTHER INFORMATION: Bul-409s Gus

<400> SEQUENCE: 4
acttacctct tatataaaaa agaaaaagtg tttctaatat atactcaatt taaataaaat      60
attttcaatc aaatttagat aacaaatact tatcaatatg aggtcaataa caataaaaaa     120
ataatgtaaa aaaaaaggag caatacataa tataagaaaa aagattaaag tgcgattatc     180
aacgagtatt ataccctaat ttgctaatat ttaaactctt atatttaagg ttatgttcac     240
aatatactta aaaagcgcta tattagagca tatattaatt aataaaaaag aaaatgctaa     300
atgatcaaaa aaattagata gaaaattaag aaaattataa tatttttta ttttaaaata     360
aattgatata ttctttattt tttagttaaa atgtattaaa gttaaaagaa taaaaatatt     420
ttaaaaaata aaataacata aataaaatat cattctaatt aaattcagac caaattttt     480
ccccagattt tggccaatac ctaaaataaa attaagttat ttttagtata ttttttttaca    540
ttgacctaca tttttctagt tttttctaaa ggagcgtgta agcgtcaacc tcattctcct     600
aattttcccc accacataaa taaaagaaa cggtagcttt tgcgtgttgt tttgctacac      660
tacacctcat tattacacgt gtcatcatat aattggctaa ccctatgagg cggtttcgtc     720
tagagtcggc catgccatct ataaaaggaa cctttctgca cctcattttt tcatcttcta     780
tctgacttct attataattt ctctcaattg cctttaaatt tctctttcaa ggttagaaat     840
cttctctatt ttttggtttt tgtctgttta gattctcgaa ttagctaagc aggtgctgtt     900
aaagccctaa aatttgagtt tttttttccgt tgttttgatg aaaaagcccc taatttgagt     960
ttttttccgt cgatttgatg ccaaaggttt aaaattagag tttttttcgtc ggtttgattc    1020
taaaggccca aaatgtgggg ttttccgggt gatttgatga taatgcccta gaatttgagt    1080
tttttatgg tggtttgatg aaaaaggtct tgaatttgat tttttttttc cggttgattt     1140
gatgaaaaag ccctagaatt tgtgattttt cgtcggtttg attctaaagc cctaaaattt     1200
gaggttttcc ggttgttttg atgaaaaagc cctaaaattt gagtttttc cccgtgtttt     1260
agattgtttg gttttaattc tcgaatcagt taatcaggga gtgtgaaaag ccctataatt    1320
tgagttttt tcgttgttcc gattgttgtt tttatgactt tgcagatgca gatctttgtg     1380
aaaactctca ccggaaagac catcacccta gaggtggaac gttctgatac aatcgacaac    1440
gttaaggctg agattcagga taaggaagga attccccgg atcagcaaag cttatcttc      1500
gccggaaagc agttggagga cggacgtact ctagctgatt acaacatcca gaaggagtct    1560
accctccatt tggttctccg tctacgtggt ggtggatccc cggtggtca gtcccttatg     1620
ttacgtcctg tagaaacccc aacccgtgaa atcaaaaaac tcgacggcct gtgggcattc    1680
agtctggatc gcgaaaactg tggaattgat cagcgttggt gggaaagcgc gttacaagaa    1740
agccgggcaa ttgctgtgcc aggcagtttt aacgatcagt cgccgatgc agatattcgt     1800
aattatgcgg gcaacgtctg gtatcagcgc gaagtcttta taccgaaagg ttgggcaggc    1860
cagcgtatcg tgctgcgttt cgatgcggtc actcattacg gcaaagtgtg gtcaataat     1920
caggaagtga tggagcatca gggcggctat acgccatttg aagccgatgt cacgccgtat    1980
gttattgccg ggaaaagtgt acgtatcacc gtttgtgtga acaacgaact gaactggcag    2040
actatcccgc cggaatggt gattaccgac gaaaacggca agaaaaagca gtcttacttc    2100
catgatttct ttaactatgc cggaatccat cgcagcgtaa tgctctacac cacgccgaac    2160
```

```
acctgggtgg acgatatcac cgtggtgacg catgtcgcgc aagactgtaa ccacgcgtct    2220
gttgactggc aggtggtggc caatggtgat gtcagcgttg aactgcgtga tgcggatcaa    2280
caggtggttg caactggaca aggcactagc gggactttgc aagtggtgaa tccgcacctc    2340
tggcaaccgg gtgaaggtta tctctatgaa ctgtgcgtca cagccaaaag ccagacagag    2400
tgtgatatct acccgcttcg cgtcggcatc cggtcagtgg cagtgaaggg cgaacagttc    2460
ctgattaacc acaaaccgtt ctactttact ggctttggtc gtcatgaaga tgcggacttg    2520
cgtggcaaag gattcgataa cgtgctgatg gtgcacgacc acgcattaat ggactggatt    2580
ggggccaact cctaccgtac ctcgcattac ccttacgctg aagagatgct cgactgggca    2640
gatgaacatg gcatcgtggt gattgatgaa actgctgctg tcggctttaa cctctcttta    2700
ggcattggtt tcgaagcggg caacaagccg aaagaactgt acagcgaaga ggcagtcaac    2760
ggggaaactc agcaagcgca cttacaggcg attaaagagc tgatagcgcg tgacaaaaac    2820
cacccaagcg tggtgatgtg gagtattgcc aacgaaccgg ataccgtcc gcaaggtgca    2880
cgggaatatt tcgcgccact ggcggaagca acgcgtaaac tcgacccgac gcgtccgatc    2940
acctgcgtca atgtaatgtt ctgcgacgct cacaccgata ccatcagcga tctctttgat    3000
gtgctgtgcc tgaaccgtta ttacggatgg tatgtccaaa gcggcgattt ggaaacggca    3060
gagaaggtac tggaaaaaga acttctggcc tggcaggaga aactgcatca gccgattatc    3120
atcaccgaat acggcgtgga tacgttagcc gggctgcact caatgtacac cgacatgtgg    3180
agtgaagagt atcagtgtgc atggctggat atgtatcacc gcgtctttga tcgcgtcagc    3240
gccgtcgtcg gtgaacaggt atggaatttc gccgattttg cgacctcgca aggcatattg    3300
cgcgttggcg gtaacaagaa agggatcttc actcgcgacc gcaaaccgaa gtcggcggct    3360
tttctgctgc aaaaacgctg gactggcatg aacttcggtg aaaaaccgca gcagggaggc    3420
aaacaatgat atcatacaac tctcctggcg caccatcgtc ggctacagcc tcgggaattg    3480
ctaccgagct cgaatttccc cgatcgttca aacatttggc aataaagttt cttaagattg    3540
aatcctgttg ccggtcttgc gatgattatc atataatttc tgttgaatta cgttaagcat    3600
gtaataatta acatgtaatg catgacgtta tttatgagat gggttttat gattagagtc    3660
ccgcaattat acatttaata cgcgatagaa aacaaaatat agcgcgcaaa ctaggataaa    3720
ttatcgcgcg cggtgtcatc tatgttacta gatcgggaat tgatccccgg gtacc         3775
```

SOLANUM BULBOCASTANUM POLYUBIQUITIN BUL409 PROMOTER AND USES THEREOF

FIELD OF THE INVENTION

The invention relates to isolated *Solanum Bulbocastanum* promoter sequences and uses thereof.

BACKGROUND OF THE INVENTION

Plant genetic engineering allows plant breeders to modify the genetic makeup of a plant precisely and predictably. Both alone and in combination with traditional plant breeding techniques, genetic engineering facilitates the creation of improved varieties faster, and with greater ease, than is possible when only traditional plant-breeding techniques are available.

Isolated plant promoters are instrumental for constructing genetically engineered plants. Typically, to produce transgenic plants, an isolated plant promoter is inserted into a vector and operably linked to a heterologous DNA sequence, thereby creating an expression construct. Plant cells are then transformed with the expression construct by any of a number of art recognized methods. The result of transformation is that the plant promoter operably linked to the heterologous DNA, is inserted into the genome of the transformed plant cell, and regulation of the heterologous DNA expression in the transformed plant cell is controlled by the promoter.

There are a variety of different approaches for producing a desired phenotype in a transgenic plant. The chosen approach typically depends on the nature of the heterologous sequences coupled to the isolated plant promoter. For example, expression of a novel gene that is not normally expressed in plant, or in a particular tissue of a plant, may confer a phenotypic change. Alternatively, the expression of a sense or an antisense construct introduced into transgenic plants can cause the inhibition of expression of endogenous plant genes. This inhibition of expression can, in turn, produce a desired phenotypic change.

To facilitate the production of precise phenotypes, it is advantageous to have available a variety of different promoters for the genetic engineering of plants. Unfortunately however, promoter elements capable of directing high levels of transgene expression are difficult to isolate. Thus, such promoters remain limited in number, and as a result, there is a continuing demand for new promoters.

An exemplary plant promoter used for plant genetic engineering is the CaMV 35S promoter. Derived from the cauliflower mosaic virus, the CaMV35S promoter is the promoter of choice for much of plant genetic engineering. Indeed, it is used in almost all genetically modified crops currently grown or tested.

The CaMV 35S promoter is a strong, constitutive promoter which delivers high expression of operably linked genes in almost any type of cell or tissue of a plant, at any developmental stage. But, despite its current popularity, a number of problems associated with use of the CaMV 35S promoter make its use less than ideal. For example, in addition to being protected by patents that limit its use in the commercial sector, use of the CaMV promoter has provoked concerns about the safety of a promoter that is derived from a virus.

Indeed, some consumers, along with a few advocacy groups, have voiced concern about the safety and environmental impact of genetically engineered food products. Typically, concerns about food safety center around the breaking and joining up of otherwise incompatible genetic material, thereby increasing the chances for horizontal transmission to unrelated species. (see e.g., Nowora, T. et al (1999). *Virology* 255, 214-20, Maiss, E., et al (1992). *J. Gen. Virol.* 73, 709-13; Meyer, M and Dessens, J. (1997). *J. Gen. Viol.* 78, 147-51).

Genetic engineering offers tremendous potential for the production of better and more plentiful products. However, genetic engineering is still a fledgling economic force in the commercial food business and so is far from reaching its full potential. Ultimately, the success or failure of genetically engineered foods depends not only on the quality or quantity of what genetically engineered plants can produce, but instead on public acceptance of the products. Therefore, producers of genetically engineered crops need to ensure that the public is comfortable with the safety of their products.

Thus, what is needed in the art, are genetically engineered foods that are readily accepted by the public. To meet the demand for safe acceptable produce, what is needed are promoters that are publicly acceptable and do not provoke safety concerns, and which at the same time, are effective at controlling gene expression and producing desired phenotypes. Such promoters should be capable of directing high levels of transgene expression, should be useful in many different applications, and should be plant derived. Such promoters would avoid or eliminate many if not all of the drawbacks associated with the most popular promoters e.g., CaMV 35S promoter, and thus would facilitate the acceptance of genetically engineered products.

Fortunately, as will be clear from the following disclosure, the present invention provides for these and other needs.

SUMMARY OF THE INVENTION

In one embodiment, the present invention provides an isolated plant Bul409 promoter comprising a nucleic acid sequence that is at least about 90% identical to nucleotides 1-771 of SEQ ID NO:1, wherein the promoter is capable of controlling transcription in a plant. In another exemplary embodiment, the isolated Bul409 promoter is at least about 95% identical to nucleotides 1-771 of SEQ ID NO:1. In another exemplary embodiment, the invention provides an isolated plant Bul409 promoter that is capable of hybridizing under stringent conditions to nucleotides 1-771 of SEQ ID NO:1, and in still another exemplary embodiment, the isolated Bul409 promoter complex has a nucleic acid sequence identical to SEQ ID NO:1.

In another exemplary embodiment, the invention provides a vector comprising an isolated plant Bul409 promoter operably linked to a heterologous nucleic acid sequence.

In another exemplary embodiment, the invention provides a transgenic plant comprising an isolated plant Bul409 promoter operably linked to a heterologous nucleic acid sequence. In one exemplary embodiment, the transgenic plant is a dicotyledonous plant.

In another exemplary embodiment, the invention provides a method for controlling transcription of a heterologous nucleic acid sequence in a plant cell, wherein the method comprises (i) transforming a plant cell with a vector comprising a Bul409 promoter operably linked to a heterologous nucleic acid sequence; and (ii) growing the transformed plant cell under conditions where the heterologous nucleic acid is expressed in the plant cell. In one exemplary embodiment, the method provides constitutive expression of the heterologous nucleic acid. In another exemplary embodiment, expression of the heterologous nucleic acid is upregulated. In still another exemplary embodiment, the expression of the heterologous nucleic acid is upregulated in response to wounding of a plant or plant part comprising the plant cell.

Other features, objects and advantages of the invention will be apparent from the detailed description which follows.

BRIEF DESCRIPTION OF THE DRAWINGS

FIG. 1 SEQ ID NO:1 Sequence of Bul409s promoter, nucleotides 1-1599. Nucleotides 1-771 Bul409s promoter 5' regulatory domain; nucleotides 1-3 ScaI half site; nucleotides 772-830 5' untranslated region; nucleotides 831-1365 intron; nucleotides 1366-1593 ubiquitin monomer; nucleotides 1594-1599 BamHI site.

FIG. 2 SEQ ID NO:2 Sequence of native Bul409 polyubiquitin gene nucleotides 1-6616. Nucleotides 1-3371 full length promoter; nucleotides 2597-2602 ScaI site 5' end 409s promoter; nucleotides 3372-3430 5' untranslated region; nucleotides 3431-3964 intron; nucleotides 3965-5335 six ubiquitin monomer polyprotein; nucleotides 5336-5338 stop codon.

FIG. 3 SEQ ID NO:3 Sequence of the full length Bul409 promoter nucleotides 1-4192. Nucleotides 1-3371 Bul409 full length 5' regulatory domain; nucleotides 2597-2602 ScaI site 5' end 409s promoter; nucleotides 3372-3430 5' untranslated region; nucleotides 3431-3964 intron; nucleotides 3965-4192 ubiquitin monomer.

FIG. 4 SEQ ID NO:4 Sequence of the Bul409s-GUS fusion transgene nucleotides: 1-3775; nucleotides 1-1593 Bul409s promoter sequence: nucleotides 1-771 409s promoter 5' regulatory domain; nucleotides 1-3 3' half ScaI site; nucleotides 772-830 5' untranslated region; nucleotides 831-1365 intron; nucleotides 1366-1593 ubiquitin monomer; nucleotides 1594-1599 BamHI Site; nucleotides 1618-3426 *E. coli* β-glucuronidase; nucleotides 3427-3429 stop codon; nucleotides 3499-3749 polyadenylation signal and *Agrobacterium* Nopaline Synthase terminator.

DETAILED DESCRIPTION OF THE INVENTION

Definitions

Figure 5:
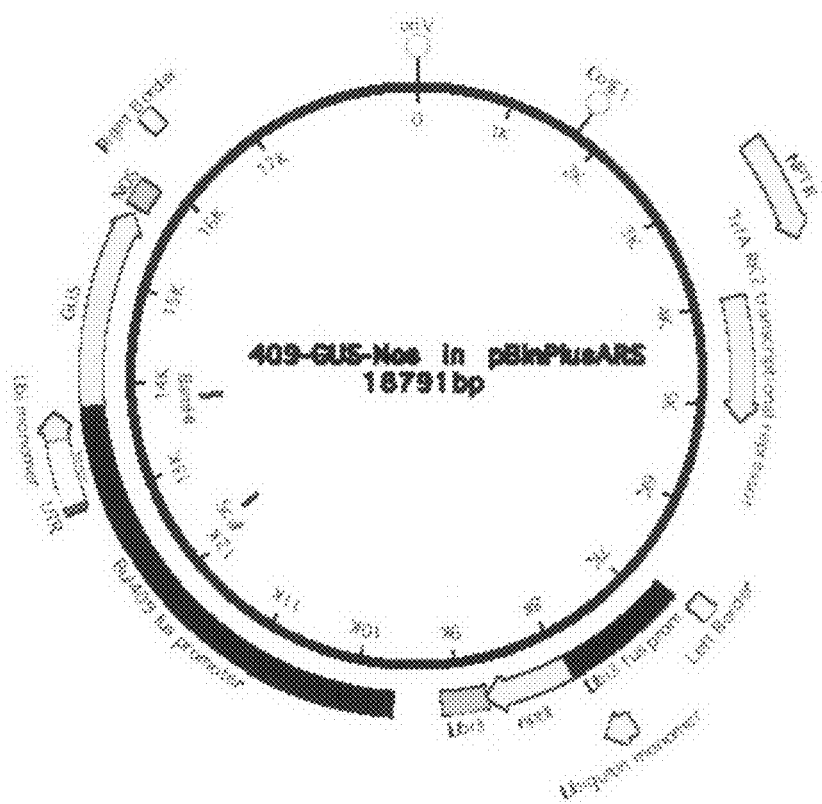
FIG. 5 Full length Bul409 promoter sequence in an expression vector.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes plants of any variety of ploidy levels, including polyploid, diploid, haploid and hemizygous.

Some exemplary plants include, but are not limited to, alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), wheat (*Triticum* spp), rice (*Oryza sativa*), barley (*Hordeum vulgare*), oats (*Avena sativa*), maize (*Zea mays*), rye (*Secale cereale*), onion (*Allium* spp), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), papaya (*Carica papaya*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* e.g., Hubbard squash (*C. Hubbard*), Butternut squash (*C. moschtata*), Zucchini (*C. pepo*), Crookneck squash (*C. crookneck*), *C. argyrosperma*, *C. argyrosperma* ssp *sororia*, *C. digitata*, *C. ecuadorensis*, *C. foetidissima*, *C. lundelliana*, and *C. martinezii*, and members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum, and laboratory plants, e.g., *Arabidopsis*.

The term "transgenic plant" as used herein refers to a plant comprising at least one heterologous nucleic acid sequence that was introduced into the plant, at some point in its lineage, by genetic engineering techniques. In an exemplary embodiment, a transgenic plant is a plant that is transformed with an expression vector comprising a Bul409 promoter nucleic acid. In another exemplary embodiment, a transgenic plant is a plant that is the progeny or decendant of a plant that is transformed with an expression vector comprising a Bul409 promoter nucleic acid and which comprises the expression vector comprising a Bul409 promoter nucleic acid. Thus, the term "transgenic plant" refers to plants which are the direct result of transformation with a heterologous nucleic acid or transgene, and the progeny and decendants of transformed plants which comprise the introduced heterologous nucleic acid or transgene.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated Bul409 promoter nucleic acid is separated from open reading frames and/or other nucleic acid sequences that flank the Bul409 promoter in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a Bul409 promoter complex sequence will anneal to a related target sequence with a higher specificity than a corresponding primer of only 15 nucleotides. Thus, in an exemplary embodiment, greater specificity of a nucleic acid primer or probe, is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid e.g., intron sequence and/or intron and ubiquitin monomer sequences as disclosed herein.

As is well known in the art, a "constitutive" promoter is a promoter that is active under most environmental and developmental conditions. An "inducible" promoter is a promoter that is active under environmental or developmental regulation, e.g., upregulation in response to wounding of plant tissues. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The term "Bul409 promoter" or "Bul409 promoter sequence" or "Bul409 promoter nucleic acid" or "Bul409 promoter complex" as used herein, refers to isolated plant promoters which comprise a nucleotide sequence identical to or substantially identical to base pairs 1-771 of SEQ ID NO:1, and which are able to control transcription of operably linked nucleic acids in plants. An exemplary Bul409 promoter is illustrated in FIG. 1. Another exemplary Bul409 promoter is illustrated in FIG. 3. Typically, isolated Bul409 promoter sequences are derived from the Bul409 gene of *Solanum Bulbocastanum* or other members of the Solanaceae family. However, isolated Bul409 promoter sequences can be isolated from any source and/or can be synthetically made, by methods known on the art (see e.g., U.S. Pat. No. 5,942,609) as long as they are substantially identical to Bul409 promoter sequences as disclosed herein. Methods for determining nucleotide sequence identity and "substantial identity" are described below. However, in general, two nucleic acid sequences are considered to be substantially identical when the two molecules or their complements hybridize to each other under stringent hybridization conditions, as described below.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a Bul409 promoter. Hybridization of the first and second nucleic acids is conducted under standard stringent conditions, e.g., high temperature and/or low salt content, which tend to disfavor hybridization of dissimilar nucleotide sequences.

The expression "control transcription", "controlling transcription" or "control of transcription" or other grammatically equivalent phrases or expressions as used herein refers to the ability of an "expression control sequence" typically a promoter, e.g., a Bul409 promoter, to direct transcription of an operably linked nucleic acid sequence. Methods for testing the activity of promoters and putative promoters in plant cells are known in the art see e.g., L. Szabados et al. (1995) Molecular Breeding 1(4):419-423 and Y. Yang et al. (2000) The Plant Journal, 22(6): 543-551. A promoter that is "able to control transcription of operably linked nucleic acids in plants" refers to promoters that can direct transcription of an operably linked nucleic acid sequence in a plant cell. In an exemplary embodiment, "controlling transcription" refers to initiating transcription. In another exemplary embodiment, "controlling transcription" refers to up-regulating transcription over a basal constitutive level of transcription.

The term "operably linked" refers to a functional linkage between a nucleic acid expression control sequence (such as e.g., a Bul409 promoter, or array of transcription factor binding sites) and a second nucleic acid sequence, wherein the expression control sequence directs expression e.g., transcription, of the nucleic acid corresponding to the second sequence. In an exemplary embodiment, a promoter e.g., a Bul409 promoter, that is "operably linked" to a heterologous nucleic acid is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter e.g., a Bul409 promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length Bul409 promoter sequence or gene sequence given in a sequence listing, or may comprise a complete Bul409 promoter sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng &

Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

In an exemplary embodiment the invention provides isolated Bul409 promoter sequences which comprise a nucleic acid sequence that is at least about 90% identical to base pairs 1-771 of SEQ ID NO:1, wherein the promoter is capable of initiating transcription in a plant. In another exemplary embodiment, the isolated Bul409 promoter is at least about 95% identical to base pairs 1-771 of SEQ ID NO:1. In another exemplary embodiment, the isolated Bul409 promoter has a nucleic acid sequence identical to SEQ ID NO:1. In still another exemplary embodiment, the isolated Bul409 promoter hybridizes to base pairs 1-771 of SEQ ID NO:1 under stringent conditions.

In other exemplary embodiments the invention provides expression vectors comprising isolated Bul409 promoter sequences, transgenic plants comprising isolated Bul409 promoter sequences, and methods for expressing heterologous nucleic acids in plants, wherein the heterologous nucleic acid is operably linked to an isolated Bul409 promoter sequence.

II. Isolating the Polyubiquitin Promoter and Constructing Expression Vectors

A. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Nucleic Acids Comprising Bul409 Promoter Sequences Plant Bul409 promoters can be isolated using any of a variety of methods known to those of skill in the art which may be used for isolation of plant promoters. For example, plant Bul409 promoters can be isolated from genomic DNA fragments encoding a plant Bul409 gene. The term "plant Bul409 gene" or "Bul409 gene" as used herein, refers to a plant genomic DNA molecule that comprises the entire Bul409 promoter region operably linked to the entire coding region (including exons and introns) for the Bul409 protein and which may also include the adjacent 3' flanking region which encodes the 3' non-translated mRNA. An exemplary "Bul409 gene" is shown in FIG. 2. The term "plant Bul409 gene fragment" or "Bul409 gene fragment" refers to a portion of the plant Bul409 gene which is less than the entire promoter and coding regions of the gene. A plant Bul409 gene fragment may comprise a promoter region operably linked to a portion of the coding region of the gene. An exemplary "plant Bul409 gene fragment" is shown in FIG. 1. Genomic fragments encoding plant Bul409 genes and Bul409 gene fragments can be prepared as disclosed below.

In an exemplary embodiment, the nucleic acid sequences comprising Bul409 promoter sequences and related nucleic acid sequences are cloned from genomic DNA libraries using labeled oligonucleotide probes. In another exemplary embodiment, the nucleic acid sequences comprising Bul409 promoter sequences and related nucleic acid sequences are cloned from genomic DNA libraries using amplification techniques and labeled oligonucleotide primers.

Plant Bul409 promoter sequences typically comprise sequences that are identical to, or show substantial sequence identity (as defined above) to nucleotides 1-771 of the *Solanum bulbocastanum* plant Bul409 promoter nucleic acid sequence depicted in SEQ ID NO:1.

Thus, plant Bul409 promoter sequences typically hybridize to base pairs 1-771 of the nucleic acid sequence of SEQ ID NO:1 under stringent hybridization conditions.

To prepare a genomic library, typically DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA encoding plant Bul409 genes and/or plant Bul409 gene fragments is identified in genomic libraries by its ability to hybridize with labeled nucleic acid probes that comprise Bul409 promoter sequences, e.g., on Southern blots. The hybridizing DNA regions are isolated by standard methods familiar to those of skill in the art. See e.g., Sambrook, et al. supra.

In an exemplary embodiment, plant Bul409 promoter sequences are isolated by screening plant DNA libraries with labeled oligonucleotide probes having sequences derived from nucleotides 1-771 of the DNA sequence of the *Solanum bulbocastanum* Bul409 promoter shown in FIG. 1, SEQ ID NO:1.

Other methods known to those of skill in the art can also be used to isolate plant DNA fragments comprising Bul409 promoters. See e.g., Sambrook, et al. for a description of other techniques for the isolation of DNAs related to DNA molecules of known sequence.

In exemplary embodiments, deletion analysis and a promoterless reporter gene (e.g., GUS) are used to identify those regions which can drive expression of a structural gene. Sequences characteristic of promoter sequences can also be used to identify the promoter. Indeed, sequences controlling eukaryotic gene expression have been extensively studied. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G, see e.g., J. Messing et al., (1983) in Genetic Engineering in Plants, pp. 221-227 Kosage, Meredith and Hollaender, eds.

Once a putative promoter sequence is identified it can be tested for promoter activity, e.g, tested for the ability to direct transcription of an operably linked nucleic acid sequence in plants. Methods for testing the activity of promoters and putative promoters in plant cells are known in the art see e.g., L. Szabados et al. (1995) Molecular Breeding 1(4):419-423 and Y. Yang et al. (2000) The Plant Journal, 22(6): 543-551.

In one exemplary embodiment, plant promoters are characterized in vivo by generating a transgenic plant which comprises an expression vector comprising a putative promoter operably linked to a heterologous nucleic acid that acts as a reporter gene e.g., a nucleic acid encoding GUS activity. The transgenic plant is then evaluated for expression of the reporter gene.

In another exemplary embodiment, *Agrobacterium* mediated transient transfection is used to assay promoter activity see e.g., Y. Yang et al. (2000) supra. As is known in the art *Agrobacterium* mediated transient transfection provides a reliable transient expression assay. Typically, a binary expression vector comprising a putative promoter and an operably linked heterologous reporter gene e.g., GUS, is introduced into an appropriate *Agrobacterium* strain, and the resulting *Agrobacterium* is used to mediate transient transformation in planta, and activity of the reporter gene, e.g., GUS is evaluated by methods well known in the art.

In another exemplary embodiment, ballistic transient transformation of plant cells or organs is used to analyse plant promoter activity (see e.g., Baum, K., et al. (1997). Plant J. 12, 463-469). In still another exemplary embodiment, promoter activity is tested by observing the ability of a nucleic acid sequence to drive the expression of green florescent protein see e.g., Harper, B. K. and Stewart J R. C. N. (2000) Plant Molecular Biology Reporter 18: 141a-141i; and Moseyko, N & L. J. Feldman (2001) Plant, Cell and Environment 24, 557-563.

Thus, sequences isolated from genomic libraries (or any other source) by virtue of their ability to hybridize to Bul409 promoter sequences, can be tested for promoter activity by methods known in the art.

Sequence Features of Bul409 Promoter Sequences

The full length Bul409 gene from *Solanum bulbocastanum* typically comprises about 6616 nucleotides. The sequence of the full length Bul409 gene is shown in FIG. 2, as SEQ ID NO:2. The 5' regulatory sequences of the full length Bul409 promoter from *Solanum bulbocastanum* span nucleotides 1-3371 of SEQ ID NO:2. A full length *Solanum bulbocastanum* promoter comprising the 5' regulatory sequences is also shown as SEQ ID NO:3 in FIG. 3. The ubiquitin polyprotein from *Solanum bulbocastanum* which comprises six ubiquitin monomers, spans nucleotides 3965-5335 of SEQ ID NO:2. A translation stop codon is present at nucleotides 5336-5338. An intron is present at nucleotides 3431 through 3964, and the 5' untranslated region spans nucleotides 3372-3430. An ScaI restriction site which marks the 5' end of the Bul409s promoter, depicted in FIG. 1 as SEQ ID NO:1, spans nucleotides 2597-2602 of SEQ ID NO:2.

A short Bul409 promoter, Bul409s, is depicted in FIG. 1 as SEQ ID NO:1. Bul409s comprises about 1599 nucleotides. Promoter sequences span nucleotides 1-771. The 5' untranslated region spans nucleotides 772-830, and an intron is present at nucleotides 831 through 1365. Nucleotides 1366-1593 code for the single ubiquitin monomer. A BamHI site is present at nucleotides 1594-1599.

In one exemplary embodiment, the Bul409 promoter sequence from *Solanum bulbocastanum*, shown in FIG. 3 as SEQ ID NO:3, controls transcription of heterologous nucleic acids in transgenic plants and transgenic plant cell lines wherein the transgenic plant or plant cell line comprise a heterologous nucleic acid operably linked to a full length Bul409 promoter. In another exemplary embodiment, the Bul409s promoter sequence, shown in FIG. 1 as SEQ ID NO:1, controls transcription of heterologous nucleic acids in transgenic plants and transgenic plant cell lines wherein the transgenic plant or plant cell line comprises a heterologous nucleic acid operably linked to a Bul409s promoter.

Various modifications can be made to the Bul409 promoters disclosed herein to provide promoters with different properties (e.g., tissue specificity, promoter strength, and the like). In an exemplary embodiment, truncated forms of a Bul409 promoter are constructed by mapping restriction enzyme sites in the promoter and then using the constructed map to determine appropriate restriction enzyme cleavage to excise a subset of the sequence. The modified promoters can then be inserted into a suitable vector and tested for their ability to drive expression of a marker gene. Tissue specificity of the modified promoters can be tested in regenerated plants.

C. Construction of Vectors Comprising Bul409 Promoter Sequences

Once a plant Bul409 promoter region has been isolated, various methods may be used to construct expression cassettes, vectors and other DNA constructs. Expression cassettes comprising Bul409 promoter sequence can be constructed in a variety of ways. The skilled artisan is well aware of the genetic elements that must be present on an expression construct/vector in order to successfully transform, select and propagate the expression construct in host cells. Techniques for manipulation of nucleic acids encoding plant Bul409 promoter sequences such as subcloning nucleic acid sequences into expression vectors, labeling probes, DNA hybridization, and the like are described generally in Sambrook, et al., supra.

In an exemplary embodiment, the Bul409 promoter sequence and a heterologous DNA sequence encoding a desired gene product are cloned into an expression vector via suitable restriction endonuclease sites such that the promoter is upstream of and in-frame with the DNA sequence. In another exemplary embodiment, various procedures, such as site directed mutagenesis are used to introduce a restriction site in a Bul409 promoter sequence. In another exemplary embodiment, various procedures, such as site directed mutagenesis are used to introduce a restriction site into heterologous DNA sequence such that the sequence can be cloned into an expression vector downstream and in-frame with the Bul409 promoter sequence. Thus, heterologous DNA sequences can be linked to the Bul409 promoter such that the expression of the heterologous sequences is controlled by the Bul409 promoter.

DNA constructs comprising a Bul409 promoter operably linked to heterologous DNA sequences can be inserted into a variety of vectors. Typically, the vector chosen is an expression vector that is useful in the transformation of plants and/or plant cells. The expression vector may be a plasmid, virus, cosmid, artificial chromosome, nucleic acid fragment, or the like. Such vectors can be constructed by the use of recombinant DNA techniques well known to those of skill in the art. The expression vector comprising a Bul409 promoter sequence may then be transfected/transformed into the target host cells. Successfully transformed cells are then selected based on the presence of a suitable marker gene as disclosed below.

A number of recombinant vectors are available to those of skill in the art for use in the stable transfection of plant cells or for the establishment of transgenic plants (see e.g., Weissbach and Weissbach, (1989) *Methods for Plant Molecular Biology*, Academic Press; Gelvin et al., (1990) *Plant Molecular Biology Manual; Genetic Engineering of plants, an Agricultural Perspective*, A. Cashmore, Ed.; Plenum: NY, 1983; pp 29 38; Coruzzi, G. et al., The Journal of Biological Chemistry, 258: 1399 (1983); and Dunsmuir, P. et al., Journal of Molecular and Applied Genetics, 2:285 (1983). As is known in the art, the choice of a vector is influenced by the method that will be used to transform host plants, and appropriate vectors are readily chosen by one of skill in the art. In an exemplary embodiment, known vectors are used to create expression constructs comprising Bul409 promoter sequences.

Typically, plant transformation vectors include one or more cloned plant genes (or cDNAs) operably linked to promoter sequences, e.g., Bul409 promoter sequences, and a selectable marker. Such plant transformation vectors also typically include a transcription initiation start site, a heterologous nucleic acid the control of whose expression is desired, a ribosome binding site, an RNA processing signal, a transcription termination site, and/or a polyadenylation signal.

In some exemplary embodiments, plant transformation vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

(i) Regulatory Elements

In addition to a Bul409 promoter or a derivative thereof, expression constructs prepared as disclosed may comprise additional elements. In an exemplary embodiment, expression constructs comprising a Bul409 promoter operably linked to a heterologous coding region also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence. In one exemplary embodiment, the intron region of the Bul409 promoter (bp 831-1365 of SEQ ID NO:1) comprises an enhancer sequence. In one exemplary embodiment, Bul409 promoter sequences are operably linked to a coding sequence in the sense orientation, such that expression with the Bul409 promoter produces the respective sense strand RNA.

In some exemplary embodiments, Bul409 promoter sequences are operably linked to a coding sequence in anti-sense orientation, such that accumulation of the respective protein encoded by the sense transcript is eliminated or decreased upon expression with the Bul409 promoter.

(ii) Terminators

Expression constructs prepared as disclosed herein typically include a sequence that acts as a signal to terminate transcription and allow for the poly-adenylation of the mRNA produced by coding sequences operably linked to the Bul409 promoter. Termination sequences are typically located in the 3' flanking sequence of a coding sequence, which will typically comprise the proper signals for transcription termination and polyadenylation. Thus, in an exemplary embodiment, termination sequences are ligated into the expression vector 3' of the heterologous coding sequences to provide polyadenylation and termination of the mRNA. Terminator sequences and methods for their identification and isolation are known to those of skill in the art, see e.g., Albrechtsen, B. et al. (1991) Nucleic Acids Res. April 25; 19(8): 1845-1852, and WO/2006/013072. In one exemplary embodiment, the transcription termination sequences comprising the expression constructs, are associated with known genes from the host organism.

(iii) Marker Genes

As noted above, plant transformation vectors typically include a selectable and/or screenable marker gene to allow for the ready identification of transformants. Exemplary selectable marker genes include, but are not limited to those encoding antibiotic resistance (e.g. resistance to hygromycin, kanamycin, bleomycin, G418, streptomycin or spectinomycin) and herbicide resistance genes (e.g., phosphinothricin acetyltransferase). Exemplary screenable markers include e.g., green florescent protein.

In an exemplary embodiment, a selectable or screenable marker gene is employed as, or in addition to, a particular gene of interest, to provide or enhance the ability to identify transformants. As is known in the art, "marker genes" are genes that impart a distinct phenotype to cells expressing the marker gene, such that transformed cells can be distinguished from cells that do not have the marker. In one exemplary embodiment, marker genes encode a selectable marker which one can "select" for by chemical means, e.g., through the use of a selective agent (e.g., a herbicide, antibiotic, or the like). In another exemplary embodiment, marker genes encode a screenable marker, which is identified through observation or testing, e.g., by "screening" (e.g., the green fluorescent protein).

Numerous selectable marker genes are known to the art. Some exemplary selectable markers are disclosed in e.g., Potrykus et al., (1985) Mol. Gen. Genet., 199:183-188; Stalker et al., (1988) Science, 242:419 422; Thillet et al., (1988) J. Biol. Chem., 263:12500 12508; Thompson et al., (1987), EMBO J 6:2519-2523; Deblock et al. (1987), EMBO J. 6:2513-2518; U.S. Pat. No. 5,646,024; U.S. Pat. No. 5,561, 236; U.S. Patent application Publication 20030097687; and Boutsalis, P., and Powles, S. B. (1995) Weed Research 35: 149-155.

Some exemplary screenable markers include, but are not limited to a β-glucuronidase (GUS) or uidA gene, see e.g., U.S. Pat. No. 5,268,463, U.S. Pat. No. 5,432,081 and U.S. Pat. No. 5,599,670; a β-gene, see e.g., Sutcliffe, (1978) Proc. Natl. Acad. Sci. USA, 75:3737-3741); β-galactosidase; and luciferase (lux) gene (see e.g., Ow et al., (1986) Science, 234:856-859; Sheen et al., (1995) Plant J., 8(5):777-784; and WO 97/41228).

Exemplary selectable or screenable marker genes also include genes which encode a "secretable marker" whose secretion can be detected as a means of identifying or selecting for transformed cells. Exemplary secretable markers include but are not limited to secretable antigens that can be identified by antibody interaction, e.g., small, diffusible proteins detectable, e.g., by ELISA; and/or secretable enzymes which can be detected by their catalytic activity. E.g., small active enzymes detectable in extracellular solution (e.g., α-amylase, β-lactamase, phosphinothricin acetyltransferase); and proteins that are inserted or trapped in the cell wall (e.g., proteins that include a leader sequence such as that found e.g., in the expression unit of extensin or tobacco PR-S).

The choice of a particular marker gene is readily made by the skilled practioner according to the needs and considerations of the particular application or use.

(iv) Other Vector Components

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a colE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to recognition site for the restriction endonucleases NotI, AatII, SacII, PmeI HindIII, PstI, EcoRI, and BamHI.

D. Plant Hosts, Plant Transformation and Plant Selection and Regeneration Techniques DNA constructs containing a Bul409 promoter operably linked to a heterologous DNA sequence can be used to transform plant cells and produce transgenic plants with desired phenotypic characteristics.

Exemplary plants for transformation with expression constructs comprising Bul409 promoter sequences include, but are not limited to; dicotyledonous species, such as e.g., tobacco (*Nicotiana* spp.), tomato (*Solanum* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*), and carrot (*Daucus carota sativa*).

Transformation and regeneration of monocotyledonous and dicotyledonous plant cells is well known in the art, see e.g., Weising et al. Ann. Rev. Genet. 22:421-477 (1988); U.S. Pat. No. 5,679,558; *Agrobacterium Protocols* Kevan M. A. Gartland ed. (1995) Humana Press Inc. and Wang, M., et al. (1998) Acta Hort. (ISHS) 461:401-408. The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see e.g., EP 295959); techniques of electroporation (see e.g., Fromm et al., (1986) Nature (London) 319:791) high-velocity ballistic bombardment with metal particles coated with the nucleic acid constructs (see e.g., Kline et al., Nature (London) 327:70 (1987), and U.S. Pat. No. 4,945,050); methods to transform foreign genes into commercially important crops, such as rapeseed (see De Block et al., Plant Physiol. 91:694 701 (1989)), sunflower (Everett et al., Bio/Technology 5:1201 (1987)), soybean (McCabe et al., Bio/Technology 6:923 (1988); Hinchee et al., Bio/Technology 6:915 (1988); Chee et al., Plant Physiol. 91:1212 1218 (1989); Christou et al., Proc. Natl. Acad. Sci. USA 86:7500 7504 (1989); EP 301749), rice (Hiei et al., Plant J. 6:271 282 (1994)), corn (Gordon-Kamm et al., Plant Cell 2:603 618 (1990); Fromm et al., Biotechnology 8:833 839 (1990)), and Hevea (Yeang, H. Y., et al., In, Engineering Crop Plants for Industrial End Uses. Shewry, P. R., Napier, J. A., David, P. J., Eds.; Portland: London, 1998; pp 55 64). Other known methods are disclosed in e.g., U.S. Pat. Nos. 5,597,945; 5,589,615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (see, e.g., EP 295959 and EP 138341). In one exemplary embodiment, Ti-derived vectors are used to transform a wide variety of higher plants, including dicotyledonous plants, such as e.g., potato, soybean, cotton, rape, tobacco, and rice (see e.g., Pacciofti et al., Bio/Technology 3:241 (1985); Byme et al., Plant Cell, Tissue and Organ Culture 8:3 (1987); Sukhapinda et al., Plant Mol. Biol. 8:209 216 (1987); Lorz et al., Mol. Gen. Genet. 199:178 (1985); Potrykus, (1985) supra; Park et al., J. Plant Biol. 38(4):365 71 (1995); and Hiei et al., Plant J. 6:271 282 (1994)).

*Agrobacterium tumefaciens*-meditated transformation techniques are well described in the scientific literature. See, e.g., Horsch et al. Science (1984) 233:496-498, and Fraley et al. (1983) Proc. Natl. Acad. Sci. USA 80:4803. Typically, a plant cell, an explant, a meristem or a seed is infected with *Agrobacterium tumefaciens* transformed with the expression vector/construct which comprises a Bul409 promoter sequence. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," Science, 233:496-498; Fraley et al., (1983) Proc. Nat'l. Acad. Sci. U.S.A. 80:4803.

All plant cells which can be transformed by *Agrobacterium* and whole plants regenerated from the transformed cells can also be transformed so as to produce transformed whole plants which contain the transferred expression vector/construct which comprises a Bul409 promoter sequence.

There are various ways to transform plant cells with *Agrobacterium*, including:
(1) co-cultivation of *Agrobacterium* with cultured isolated protoplasts,
(2) transformation of cells or tissues with *Agrobacterium*, or
(3) transformation of seeds, apices or meristems with *Agrobacterium*.

Method (1) requires an established culture system that allows culturing protoplasts and plant regeneration from cultured protoplasts. Method (2) requires (a) that the plant cells or tissues can be transformed by *Agrobacterium* and (b) that the transformed cells or tissues can be induced to regenerate into whole plants. Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may also be used.

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, all of which are incorporated herein by reference. Regeneration can also be obtained from plant callus, explants, organs, or parts thereof. Such regeneration techniques are described generally in Klee et al. Ann. Rev. of Plant Phys. 38:467-486 (1987).

One of skill will recognize that, after an expression cassette comprising Bul409 promoter sequences is stably incorporated in transgenic plants and confirmed to be operable, it can be introduced into other plants by sexual crossing. Any of a number of standard breeding techniques can be used, depending upon the species to be crossed.

The skilled artisan will recognize that different independent transformation events will result in different levels and patterns of expression (Jones et al., EMBO J. 4:2411 2418 (1985); De Almeida et al., Mol. Gen. Genetics 218:78 86 (1989)), and thus that multiple events will likely need to be screened in order to obtain lines displaying the desired expression level and pattern. Exemplary method for screening transformation events may be accomplished e.g., by Southern analysis of DNA blots (Southern, (1975) J. Mol. Biol. 98: 503), Northern analysis of mRNA expression (Kroczek, J., (1993) Chromatogr. Biomed. Appl., 618(1 2): 133 145), Western analysis of protein expression, and/or phenotypic analysis e.g., resistance to an herbicide can be detected by treatment with the herbicide. Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. Alternatively, a novel protein product with enzymatic activity can be measured in an enzyme assay. In another exemplary embodiment, protein expression is quantitated and/or detected in different plant tissues using a reporter gene, e.g., GUS.

Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

E. Expression of Heterologous Nucleic Acids in Transformed Plants

The introduction of expression vectors into plants and plant cells as disclosed herein is useful for the introduction of one or more new traits to a host plant cell. There are a variety of different approaches one can use to produce a desired phenotype in transgenic plants. In an exemplary embodiment, using methods described herein, one can operably link a heterologous gene to a Bul409 promoter sequence and transform plant cells. Transgenic plants can be produced from the transformed plant cells so that the heterologous gene product is produced in certain tissues (e.g., leaves, fruit) of a transgenic plant. In this context, the term "heterologous gene" refers to a gene that is not normally present in a plant or which, if present, is not normally expressed in a particular plant cell tissue. The expression of the gene can result in the production of a protein that confers an altered phenotype on a transgenic plant. In some exemplary embodiments, a Bul409 promoter sequence operably linked to a heterologous gene is used to create transgenic plants in which heterologous nucleic acid sequences are expressed at higher or lower levels than normal. In another exemplary embodiment a heterologous nucleic acid operably linked to Bul409 promoter sequences, is introduced into a transgenic plant to modify the rate, timing, amount and/or quality of the expression of the heterologous nucleic acid.

A variety of genes capable of altering a plant phenotype can be expressed under control of Bul409 promoter sequences. Suitable genes include, but are not limited to: genes for herbicide resistance; genes for fungal disease resistance (e.g., chitinases and glucanases); genes for bacterial disease resistance (e.g., cecropins); and genes for insect resistance (e.g., *B. thuringiensis* toxin). Since, in some exemplary embodiments, a Bul409 promoter sequence provides injury-regulated as well as general expression, genes affecting fruit development could also be usefully expressed. For example, in an exemplary embodiment, a Bul409 promoter sequence can be operably linked to, e.g., genes for ripening or degradation (e.g., Acc oxidase, Acc synthase, polygalacturonase, phytoene synthase); genes for color; or genes for sweetness.

One of skill will recognize that proteins have different domains which perform different functions. Thus, gene sequences operably linked to a Bul409 promoter sequence need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing a Bul409 promoter sequence operably linked to a heterologous DNA sequence can also be used in a number of techniques to suppress expression of endogenous plant genes, e.g., sense or antisense suppression. In antisense technology, a nucleic acid segment from the desired plant gene is cloned and operably linked to a Bul409 promoter sequence such that the anti-sense strand of RNA will be transcribed. The construct is then transformed into plants and the anti-sense strand of RNA is produced. In plant cells, it has been shown that anti-sense RNA inhibits gene expression; see, e.g., Sheehy et al., Proc. Nat. Acad. Sci. USA, 85:8805-8809 (1988), and Hiatt et al., U.S. Pat. No. 4,801, 340 which are incorporated herein by reference.

The nucleic acid segment to be introduced in antisense suppression generally will be substantially identical to at least a portion of the endogenous gene or genes to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides is used, though in some exemplary embodiments a sequence of at least about 100 nucleotides is used. In other exemplary embodiments, a sequence of at least about 200 nucleotides is used, and in still other exemplary embodiments, a sequence of at least about 500 nucleotides is used.

In an exemplary embodiment catalytic RNA molecules are expressed under control of a Bul409 promoter sequence. Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozyme is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is disclosed in e.g., Haseloff et al. Nature, 334:585-591 (1988).

An exemplary method of suppression is sense suppression. Introduction of a nucleic acid configured in the sense orientation has been shown to be an effective means by which to block the transcription of target genes. For examples of the use of this method to modulate expression of endogenous genes see, Napoli et al., The Plant Cell 2:279-289 (1990), and U.S. Pat. No. 5,034,323. In an exemplary embodiment, sense suppression is used as a method for ripening control (e.g., Acc oxidase or Acc synthase), sweetness control (e.g., ADPG pyrophosphorylase), or color modification (e.g., chalcone synthase); see e.g., U.S. Pat. No. 5,034,323.

Generally, in sense suppression, some transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, though about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence whose expression is under transcriptional control of a Bul409 promoter sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

In one exemplary embodiment, the heterologous nucleic acid sequences under regulatory control of the Bul409 promoter sequences are constitutively expressed. In another exemplary embodiment, heterologous nucleic acid sequences under regulatory control of the Bul409 promoter sequences are induced. In still another exemplary embodiment, the heterologous nucleic acid sequences under regulatory control of the Bul409 promoter sequences which are induced are upregulated. In another exemplary embodiment, the heterologous nucleic acid sequences under regulatory control of Bul409 promoter sequences are upregulated in response to wounding.

Figure 8A:
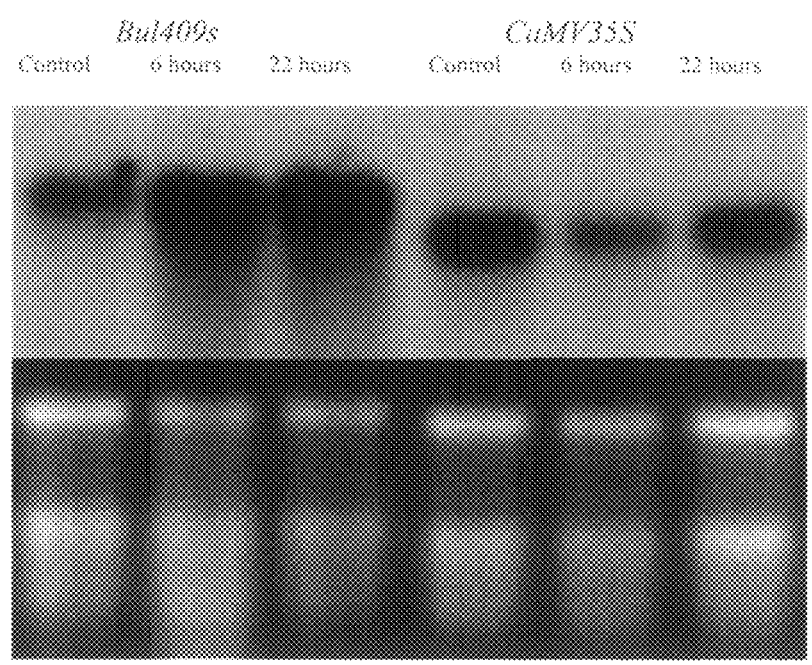
FIG. 8 Wound-induced expression of Bul409s-GUS and CaMV35S-GUS in potato leaves (8A), and tubers (8B).
Figure 8B:
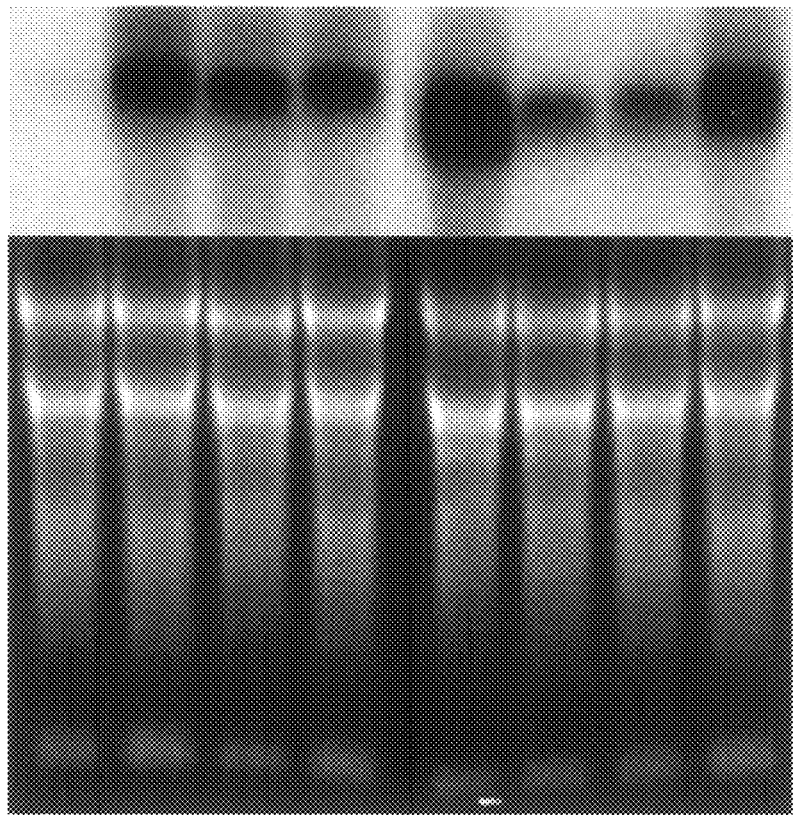

The increase in transgene expression in response to injury (see e.g., FIGS. 8 A, and B), provides a means for minimizing or curing disorders associated with plant injury. For example, a variety of economically significant disorders of crop plants are linked to plant injury e.g., in potato, tuber injury can result in bacterial and fungal infection. Thus, directly depositing a heterologous gene product at sites of injury, wherein the gene product protects against diseases and disorders associated with an injury, is but one of many useful applications for which Bul409 promoters are utilized.

Thus, in an exemplary embodiment, an expression vectors comprising a Bul409 promoter operably linked to a heterologous nucleic acid encoding a protective gene product is used to directly deposit the protective gene product at sites of injury. In one exemplary embodiment, a protective gene product is an antimicrobial gene product. Exemplary "antimicrobial gene products" include, but are not limited to: lytic peptides as disclosed in e.g., U.S. Pat. No. 6,084,156; plant antimicrobial peptides (see e.g., Broekaert, W. F., et al. (1997 Crit. Rev. Plant Sci. 16:297-323) and synthetic antimicrobial peptides (see e.g., Bessalle, R., et al. (1993). J. Med. Chem. 36:1203-1209; Arrowood, M. J., et al., (1991) J. Protozool. 38: 161s; and Jaynes, J. M., et al., (1988) FASEB J. 2: 2878).

Kits

In an exemplary embodiment, kits comprising Bul409 expression vectors are provided for expressing heterologous nucleic acids in plant cells. The kits typically include, inter alia, an expression vector comprising a Bul409 promoter and written instructions for using the kit to express heterologous nucleic acid sequences in plants and/or plant cells.

The following examples are offered to illustrate, but not to limit the invention.

EXAMPLES

Example 1

The following example illustrates and exemplary method by which Bul409 promoter sequences are isolated from a bacterial artificial chromosome library.

A *Solanum bulbocastanum* Bacterial Artificial Chromosome (BAC) library (see, Song, J, F Dong, and J Jiang. (2000) Genome 43: 199-204) was probed with random primed coding sequence from the highly expressed potato polyubiquitin cDNA ubi9 (see, Garbarino, J. E., D. R. Rockhold, and W. R. Belknap (1992) Plant Mol Biol 20: 235-44). Hybridizing BACs were identified and characterized by restriction enzyme analysis. BACs displaying distinct ubiquitin-hybridizing restriction band profiles and patterns indicating a single ubiquitin-hybridizing locus were selected for further characterization. The Bul409 BAC contained and approximately 100 kb insert. The polyubiquitin-hybridizing restriction fragment was subcloned and subjected to sequence analysis. The sequence of the Bul409 polyubiquitin gene is shown in FIG. 2. Pustell matrix analysis (see, Pustell J, Kafatos F C 1982 *Nucleic Acids Res.* 1982 Aug. 11; 10(15):4765-4782 and *Nucleic Acids Res.* 1982 Jan. 11; 10(1):51-59) was used to compare DNA sequences (MacVector8.0). Similar sequences in the available database were identified using the BLAST Network Service of the National Center for Biotechnology Information (see Altschul et al. 1990 supra).

Example 2

Figure 6:
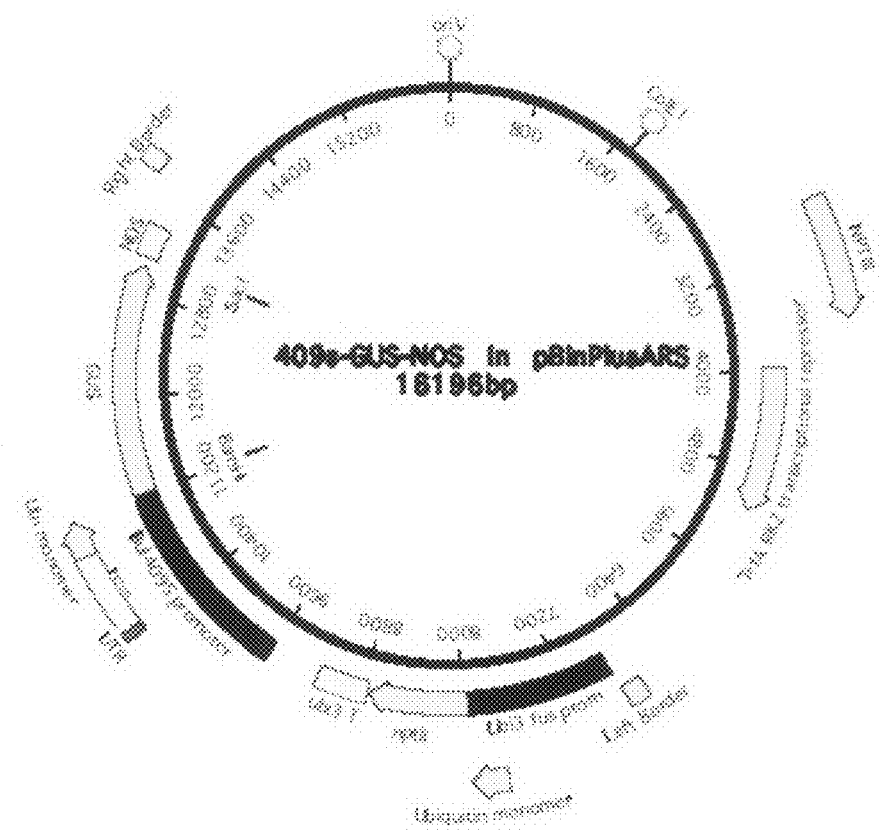
FIG. 6 Illustrates the Bul409s promoter sequence in an expression vector.

The following example illustrates an exemplary method for the construction of expression vectors comprising Bul409 promoter sequences (Bul409 see e.g., FIG. 5, and Bul409s vectors see e.g., FIG. 6).

Two Bul409 expression vectors for chimeric genes were constructed. The first (Bul409-GUS) contains the full length Bul409 promoter sequence indicated in FIG. 3 and SEQ ID NO:3. This promoter comprises the full-length promoter, intron and first ubiquitin monomer. This construct was initiated by generating a 1.8 kb PCR product from the bul409 genomic subclone employing 5' CCGGATCCAATATTACT-TAAATATCATGAAATAAACTA, (SEQ ID NO:5) and 3' CCGGATCCACCACCACGTAGACGG, (SEQ ID NO:6). Both primers contain 5' BamHI sites, the location of the BamHI site on the 3' primer allows construction of translational fusions identical to those employed previously (see, Garbarino and Belknap (1994) Plant Mol Biol 24(1): 119-27; Garbarino et al. (1995) Plant Physiol 109(4): 1371-1378). The Bul409 expression vector was constructed by fusing the 3' end of bul409 (3.3 kb HindIII/XbaI, FIG. 2) to the 0.9 kb XbaI/BamHI from the above PCR product (containing 5'-UTR, intron, ubiquitin monomer) and the GUS-NOS (*Agrobacterium* nopaline synthase polyadenylation signal) sequence employed previously (see, Garbarino and Belknap 1994 supra; Garbarino, et al. 1995 supra) in BluescriptII SK(+). The resulting transgene with a 3.4 kb promoter, 536 bp intron and ubiquitin monomer fused to GUS-NOS was then mobilized into the binary plant transformation vector pBIN-Plus/ARS (see, McCue, et al. (2006) Phytochemistry 67(15): 1590-7).

The second transgene (see Bul409s-GUS, FIG. 4, and SEQ ID NO:4, and FIG. 6) was prepared as follows. 2.6 kb at the 5' end of the Bul409 promoter was deleted by fusing unique HinDIII and ScaI sites in the Bul409-GUS binary vector (FIG. 5). Transgenes were mobilized into potato cv. Lenape via *Agrobacterium*-mediated transformation (see Snyder and Belknap (1993) Plant Cell Reports 12: 324-327).

Example 3

Figure 7A:
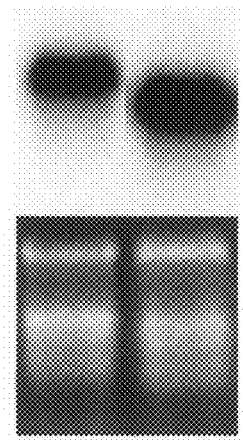
FIG. 7 Control transcription of Bul409s-GUS and CaMV35S-GUS in potato leaves (7A) and tubers (7B). GUS activity in leaves (7C).
Figure 7B:
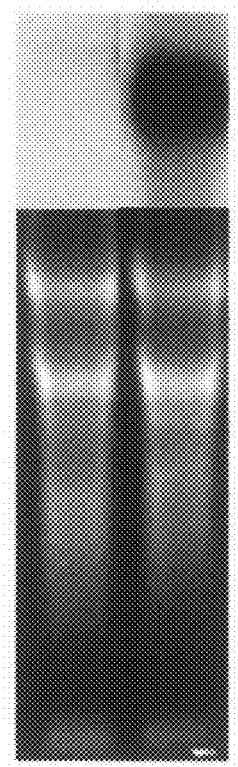
Figure 7C:
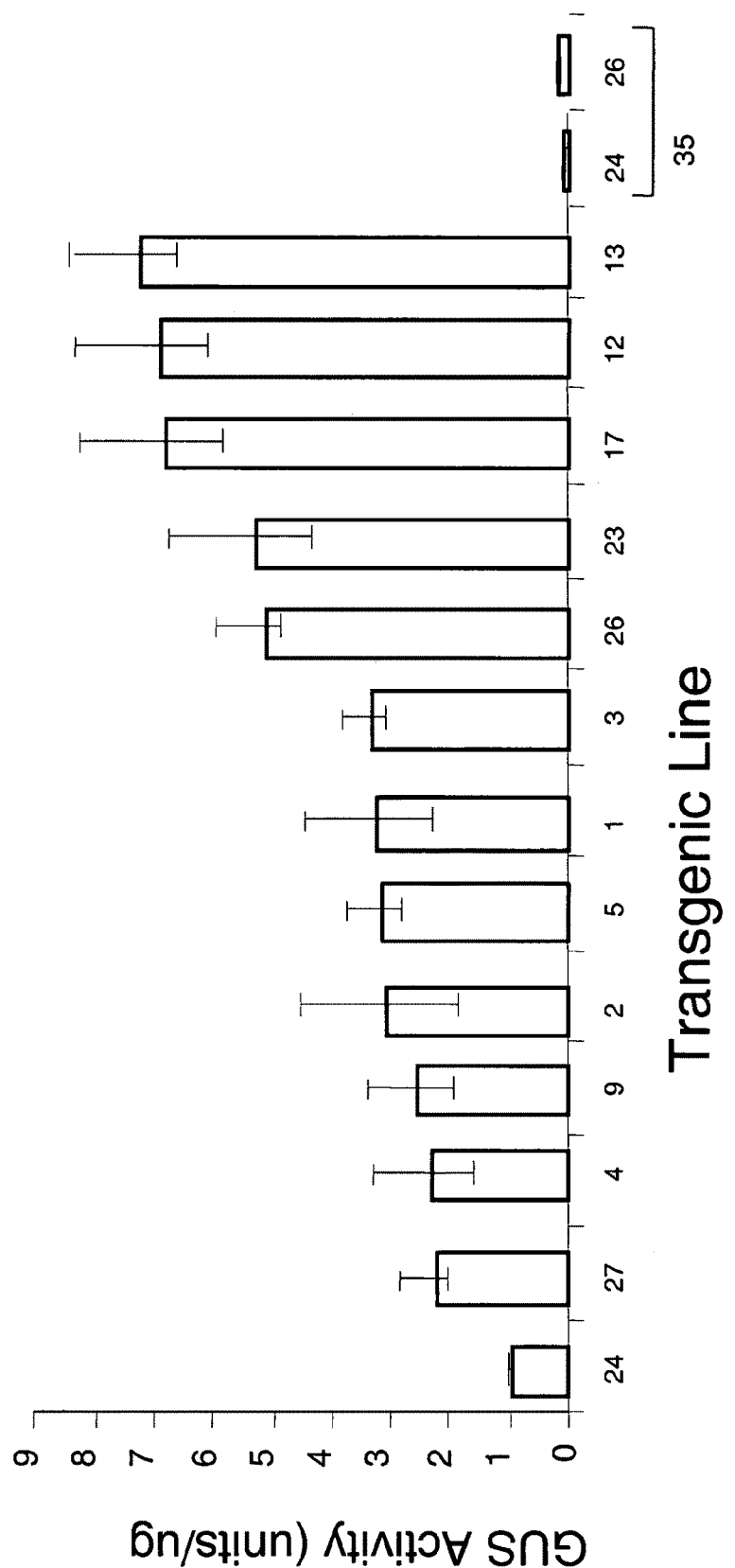

The following example illustrates that Bul409 promoter sequences efficiently control expression of GUS gene sequences when GUS gene sequences are operably linked to a Bul409 promoter sequence. A GUS-Bul409 fusion gene was introduced into potato plant cells by *Agrobacterium* mediated transformation. Expression was then examined in leaves and tubers. The results are shown in FIG. 7. Total RNA was prepared from leaves and tubers. RNA was fractionated by agarose gel electrophoresis, and transferred to a nylon membrane and hybridized with a random primed double stranded GUS probe. FIG. 7A show expression of GUS sequences in operable linkage to the Bul409s promoter sequence (SEQ ID NO:1) in leaves and 7B shows expression in tubers. Expression levels of the Bul409s promoter are compared to expression of a corresponding CaMV-GUS fusion.

Example 4

The following example illustrates the induction of expression of a Bul409-GUS fusion gene in response to wounding. The results are shown in FIG. 8.

Potato leaf tissues were wounded using a hemostat and tuber tissues were wounded by cutting into discs as described previously (see, Garbarino and Belknap (1994), supra; Garbarino, et al. (1995), supra). Total RNA was prepared from control and wounded leaves and tubers at times indicated. RNA was fractionated by agarose gel electrophoresis, and transferred to a nylon membrane and hybridized with a random primed double stranded GUS probe. In untreated transgenic leaves, the Bul409s promoter directs expression of GUS mRNA at levels similar to the CaMV35S promoter (FIG. 8A) and expression is moderately increased by wounding. In contrast, levels of expression in unwounded tubers are lower and significantly induced by injury (FIG. 8B), similar to the ubi7 profile (see Garbarino, et al. (1995) supra).

Example 5

The following example illustrates the relative expression of transgene products in operable linkage to a Bul409s promoter (SEQ ID NO:1) as compared to the CaMV35S promoter.

Transgenic Bul409s-GUS (FIG. 4 and SEQ ID NO:4) and CaMV35S-GUS plants were constructed by transforming plants with the expression vectors described in Example 2, by methods known in the art (see e.g., (Jefferson, et al. (1986) PNAS USA 83(22):8447-8451; Garbarino, et al. 1995, supra) Leaf tissues were taken from 15-week-old plants from the greenhouse. Individual transgenic lines were sampled in triplicate, and assayed for GUS activity (pmol/min/ug protein) as described previously (Jefferson, et al. 1986; Garbarino, et al. 1995, supra). As shown in FIG. 7A, in plant leaves the Bul409s promoter out-performed the CaMV35S promoter. Standard deviations were determined using Excel (Microsoft).

The GUS marker gene in the Bul409s-GUS (FIG. 4 and SEQ ID NO:4) transgene is transcribed "in frame" with the first ubiquitin monomer, translation of the mature mRNA from this transgene results in the synthesis of a ubiquitin-GUS polyprotein, which is rapidly processed in the plant cell releasing free GUS protein. As is known in the art, this type of translational fusion results in high levels of expression of GUS activity (see, Garbarino, et al. 1995 supra; Hondred Plant Physiol. 119(2): 713-724; Plesse, et al. (2001) Plant Mol. Biol. 45(6):655-657). Results shown in FIG. 7C reveal that in potato leaves GUS activity is much higher when transcription and expression are driven by the Bul409 promoter, than when transcription and expression are driven by the CaMV promoter.

Example 6

The following example illustrates expression of GUS gene sequences under control of a Bul409 promoter in onion, a monocotyledonous plant.

The Bul409s-GUS (FIG. 4 and SEQ ID NO:4) transgene was biolictically introduced into onion. This construct was coated onto Biorad 1 micron diameter gold beads Gun (Biorad, Hercules, Calif.) and accelerated using a PDS-1100 Gene Gun (Biorad, Hercules, Calif.) uses helium pressure. The target, onion peel slices, was 13 cm from the stop screen. Tissue was incubated for 18 hours (24 degrees Celsius in the dark). The tissue was then stained using X-gluc (5-bromo-4-chloro-3-indolyl-¾-D-glucuronic acid cyclohexylammonium) and incubated overnight at 37 degrees Celsius as reported by Jefferson et al. (1987) EMBO J 6: 3901-3907. Blue staining cells, which indicate GUS expression, were easily observed.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for making a transgenic plant, the method comprising:
(i) transforming a plant, plant part, or plant cell with an expression vector comprising an isolated plant Bul409 promoter operably linked to a heterologous nucleic acid sequence, wherein the isolated plant Bul409 promoter comprises a nucleic acid sequence that is identical to nucleotides 1-771 of SEQ ID NO:1 and wherein the isolated plant Bul409 promoter controls transcription of the heterologous nucleic acid in a plant,
(ii) selecting transformants comprising the expression vector which comprises the isolated plant Bul409 promoter operably linked to the heterologous nucleic acid sequence, and
(ii) growing the transformed plant, plant part, or plant cell into a whole plant, thereby producing a transgenic plant.

2. The method of claim 1, wherein the method further comprises:
(iv) conducting a sexual cross with the transgenic plant,
(v) obtaining seed from the sexual cross,
(vi) growing the seed from the sexual cross, and
(vii) selecting plants grown from the seed of the sexual cross which comprise the expression vector comprising the isolated plant Bul409 promoter operably linked to the heterologous nucleic acid sequence, wherein the isolated plant Bul409 promoter comprises a nucleic acid sequence that is identical to nucleotides 1-771 of SEQ ID NO:1 thereby producing a transgenic plant.

3. A transgenic plant comprising an isolated plant Bul409 promoter operably linked to a heterologous nucleic acid sequence
wherein,
the isolated plant Bul409 promoter comprises a nucleic acid sequence that is identical to nucleotides 1-771 of SEQ ID NO:1, and
wherein
the isolated plant Bul409 promoter sequence controls transcription in a plant.

4. The transgenic plant of claim 3, wherein the plant is a dicotyledonous plant.

5. The transgenic plant of claim 4, wherein the dicotyledonous plant is a member selected from the group consisting of: alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), and lettuce (*Lactuea sativa*).

6. A transgenic descendant of the transgenic plant of claim 3, wherein the transgenic descendant comprises the isolated plant Bul409 promoter operably linked to the heterologous nucleic acid sequence.

7. A method for controlling transcription of a heterologous nucleic acid sequence in a plant or plant cell, the method comprising:
  (i) transforming a plant or plant cell with an expression vector comprising an isolated plant Bul409 promoter operably linked to the heterologous nucleic acid sequence, wherein the isolated plant Bul409 promoter comprises a nucleic acid sequence that is identical to nucleotides 1-771 of SEQ ID NO:1 thereby producing a transformed plant or plant cell; and
  (ii) growing the transformed plant or plant cell under conditions where the isolated plant Bul409 promoter controls transcription of the heterologous nucleic acid in the plant or plant cell.

8. The method of claim 7, wherein the transcription of the heterologous nucleic acid is induced.

9. The method of claim 8, wherein the transcription is induced in response to wounding of a plant or plant part which comprises the transformed plant cell.

10. The method of claim 9, wherein the heterologous nucleic acid sequences encodes an antimicrobial gene product.

11. The method of claim 7, wherein the transcription of the heterologous nucleic acid up-regulates expression of an endogenous nucleic acid.

12. The method of claim 7, wherein the transcription of the heterologous nucleic acid down-regulates the expression of an endogenous nucleic acid.

13. An expression cassette comprising an isolated plant Bul409 promoter operably linked to a heterologous nucleic acid sequence
wherein,
  the isolated plant Bul409 promoter comprises a nucleic acid sequence that is identical to nucleotides 1-771 of SEQ ID NO:1, and
wherein
  the isolated plant Bul409 promoter sequence controls transcription in a plant.

14. The expression cassette of claim 13, wherein the isolated plant Bul409 promoter operably linked to the heterologous nucleic acid sequence is a member selected from the group consisting of SEQ ID NO:1 and SEQ ID NO:3.

15. The transgenic plant of claim 3, wherein the isolated plant Bul409 promoter operably linked to the heterologous nucleic acid sequence is a member selected from the group consisting of SEQ ID NO:1 and SEQ ID NO:3.

16. The method of claim 1, wherein the isolated plant Bul409 promoter operably linked to the heterologous nucleic acid sequence is a member selected from the group consisting of SEQ ID NO:1 and SEQ ID NO:3.

17. The method of claim 7, wherein the isolated plant Bul409 promoter operably linked to the heterologous nucleic acid sequence is a member selected from the group consisting of SEQ ID NO:1 and SEQ ID NO:3.

18. An expression vector comprising the expression cassette of claim 13.

* * * * *